(12) United States Patent
Tang et al.

(10) Patent No.: US 10,011,562 B2
(45) Date of Patent: Jul. 3, 2018

(54) LONG-CHAIN DIMETHYLANILINE DERIVATIVE COMPOUNDS, THEIR PREPARATION METHODS, SELF-ASSEMBLED TEXTURES, AND USES THEREOF

(71) Applicant: WEST CHINA HOSPITAL, SICHUAN UNIVERSITY, Chengdu, Sichuan (CN)

(72) Inventors: Lei Tang, Sichuan (CN); Jin Liu, Sichuan (CN); Wensheng Zhang, Sichuan (CN); Jun Yang, Sichuan (CN); Bowen Ke, Sichuan (CN); Qinqin Yin, Sichuan (CN)

(73) Assignee: WEST CHINA HOSPITAL, SICHUAN UNIVERSITY, Chengdu, Sichuan (CN)

( * ) Notice: Subject to any disclaimer, the term of this patent is extended or adjusted under 35 U.S.C. 154(b) by 0 days.

(21) Appl. No.: 15/327,962

(22) PCT Filed: Jul. 22, 2015

(86) PCT No.: PCT/CN2015/084760
§ 371 (c)(1),
(2) Date: Jan. 20, 2017

(87) PCT Pub. No.: WO2016/015581
PCT Pub. Date: Feb. 4, 2016

(65) Prior Publication Data
US 2017/0204053 A1    Jul. 20, 2017

(30) Foreign Application Priority Data
Aug. 1, 2014   (CN) .......................... 2014 1 0373447

(51) Int. Cl.
*C07C 237/04*   (2006.01)
*C07C 237/16*   (2006.01)
*C07C 231/12*   (2006.01)

(52) U.S. Cl.
CPC .......... *C07C 237/04* (2013.01); *C07C 231/12* (2013.01); *C07C 237/16* (2013.01)

(58) Field of Classification Search
CPC .... C07C 237/04; C07C 231/12; C07C 237/16
See application file for complete search history.

(56) References Cited

U.S. PATENT DOCUMENTS 3,998,815 A * 12/1976 Bodor .................. C07D 213/80
544/351

FOREIGN PATENT DOCUMENTS

| CN | 1989099 A | 6/2007 |
|---|---|---|
| CN | 103601650 B | 8/2014 |

OTHER PUBLICATIONS

Nielsen, A., B., et al., Bioreversible quaternary N-acyloxy methyl derivatives of the tertiary amines bipivacaine andlidocaine-synthesis aqueous solubilty and stability in buffer, human plasma and simulated intestinal fluid, 2005, European Journal of Pharmaceutical Sciences, vol. 24, pp. 433-440 (Year: 2005).*

(Continued)

*Primary Examiner* — Yate' K Cutliff
(74) *Attorney, Agent, or Firm* — Novick, Kim & Lee, PLLC; Allen Xue

(57) ABSTRACT

The present invention relates to long-chain dimethylaniline derivative compounds, their preparation methods, self-assembled texture, and uses thereof. Said compounds show ultralong acting anaesthetic effect, and belong to N-diethylaminoacetyl-2,6-dimethylaniline compounds, having a structure according to formula (I). Said compounds may (Continued)

self-assemble into micelle or gel in an aqueous solvent, and exert an in vivo elongated local anesthetic actions. Local anesthesia and/or analgesic activity can last more than 72 hours. The biomaterials can self-assemble into micelles or gels in water and have local anesthetic effect, as well as can further be used as the coating of medicinal bioactive molecules for treatment of pain, itching and the like and/or the drug carriers, together with as pharmaceutical adjuvants for delivery system. Thus, said materials have a favorable perspective.

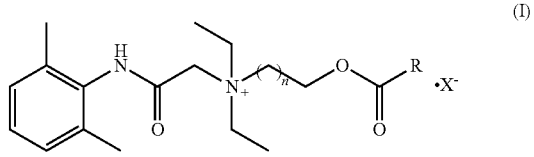

(I)

11 Claims, 10 Drawing Sheets

(56) References Cited

OTHER PUBLICATIONS

Bodor, N., Soft Drugs, 3. A New Class of Anticholinergic Agents, 1980, J. Med. Chem., vol. 23, No. 5, pp. 474-480 (Year: 1980).*

B. Nicholas, "Soft Drugs, 3, a New Class of Anticholinergic Agents",Journal of Medicinal Chemistry, vol. 5, No. 23, Dec. 31, 1980, pp. 474-480.

A. B. Nielsen et al., "Bioreversible quaternary Nacyloxymethyl derivatives of the tertiary amines bupivacaine and lidocainesynthesis, aqueous solubility and stability in buffer, human plasma and simulated intestinal fluid", European Journal of Pharmaceutical Sciences, vol. 24, No. 5, Dec. 20, 2004 , pp. 433-440.

Kenneth R. Courtney, "Mechanism of Frequency-Dependent Inhibition of Sodium Currents in Frog Myelinated Never by the Lidocaine Derivative GEA 968" The Journal of Pharmacology and Experimental Therapeutics 1975, vol. 195, No. 2, pp. 225-236.

Craig R. Ries et al. "QX-314 Produces Long-lasting Local Anesthesia Modulated by Transient Receptor Potential Vanilloid Receptors in Mice", Anesthesiology 2009, vol. 111, pp. 122-126.

Itay Sagie et al. "Prolonged Sensory-selective Nerve Blockade", PNAS, Feb. 23, 2010, vol. 107, No. 8, pp. 3745-3750.

* cited by examiner

LONG-CHAIN DIMETHYLANILINE DERIVATIVE COMPOUNDS, THEIR PREPARATION METHODS, SELF-ASSEMBLED TEXTURES, AND USES THEREOF

TECHNICAL FIELD

The present invention relates to dimethylaniline derivative compounds with potent ultralong acting anesthetic effects, their preparation methods, self-assembled textures and uses thereof.

BACKGROUND ART

Local anesthetics are drugs that can reversibly block generation and transmission of sensory nerve impulses at local administration position, and provide pain relief for local tissues under conditions of keeping people or animals awake. The action of local anaesthetics is related to the diameter of nerve cells or nerve fibers, as well as anatomical features of nerve tissues. In general, nerve fiber terminals, ganglias, and synapses of central nervous system are the most sensitive to local anesthetics, and smaller-diameter fibers are more easily blocked compared with those larger fibers. Local anaesthetics can act on postganglionic fibres of unmyelinated sympathetic and parasympathetic nerves at low concentration. When acting on mixed nerves, persistent dull pain firstly disappeared, then transient sharp pain, following by loss of cold sensation, warm sensation, touch sensation, pressure sensation, as well as occurrence of motor paralysis. Currently, it is well-known that the action mechanism of local anesthetics is blocking voltage-gated $Na^+$ channels of nerve cell membranes, then producing conduction block and local anesthetic effects.

In general, effects of local anesthetics limit to the administration position, and then the effect is fast lost as diffusion of drugs. If realizing long-acting local anesthetic effects is required, dosage of drug need further increase, except for optimizing molecular structures of local anesthetics. At present, local anesthetics clinically used are all molecules without electric charges, and can just exert local anesthesia and analgesia up to 8 hours. Thus, that can not satisfy demands of long-acting local anesthesia exceeding 72 hours. Consequently, there is an urgent need for a new type long-acting local anesthesia with more than 72 hours effects.

Most current local anesthetic drugs often contain at least one N atom from tertiary amine, and further alkyl substitution can produce corresponding quaternary ammonium salts, allowing the molecules have electric charges, thus it is not easy to pass through cell membranes. The ethyl quaternary ammonium salts of N-diethylaminoacetyl-2,6-dimethylanilines, called QX314, is a quaternary ammonium compound early reported with local anesthetic effects. However, due to the strong polarity of QX314 molecules, it can not pass through cell membranes and fast produce strong local anesthetic effects. Thus, QX314 can not be directly used in clinic. But QX314 shows a significant inhibitory on the target points $Na^+$ channels situated in the inside of cell membranes. Once passed through membranes, QX314 can potently inhibit $Na^+$ channels in the membranes, and QX314 in cell membranes hardly diffuses to out of cells, thus lasting anesthetic action can be obtained (Courtney K R. *J Pharmacol Exp Ther.* 1975, 195:225-236). Currently, many researches indicate QX314 can get into cell membranes, and produce long-time anesthesia (Craig R. Ries. *Anesthesiology* 0.2009; 111:122-126). Recent investigation has shown that with the addition of surface-active agent or with the help of forming micelles, QX314 can be assisted to enter membranes and cause local anesthetic actions lasting more than 8 hours (Daniel S. Kohane, *PNAS.* 2010; 107: 3745-3750).

DESCRIPTION OF THE INVENTION

Based on above mention, the present invention firstly provides long-chain dimethylaniline derivative compounds with ultralong acting anesthetic effects, and further provides their preparation methods, as well as self-assembled textures and uses thereof.

Long-chain dimethylaniline derivative compounds of the present invention, with ultralong acting anesthetic effects, are N-diethylaminoacetyl-2,6-dimethylaniline derivative compounds, having a structure represented by formula (I):

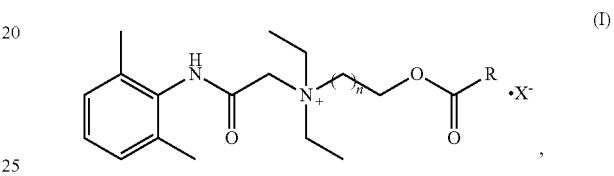

in the formula, X is selected from the group consisting of halogens and pharmaceutically acceptable anions; R is selected from the group consisting of straight chain or branch chain, substituted or unsubstituted, saturated or unsaturated $C_{2-30}$ alkyls and $C_{2-30}$ alkoxys; n represents an integer selected from 1, 2, 3, and 4.

For compounds represented by above general formula (I), the compounds having preferable structures include those in which R is $C_{12-30}$ alkoxys or alkyls and n=1; or in which R is $C_{2-11}$ alkoxys or alkyls and n=1.

The general preparation method for formula (I) compounds according to the present invention includes the following procedures:

Compound IV reacts with corresponding raw material straight chain or branch chain $C_{2-30}$ alkanols or carboxylic acid compounds (V), to provide the target compound (I), with following steps:

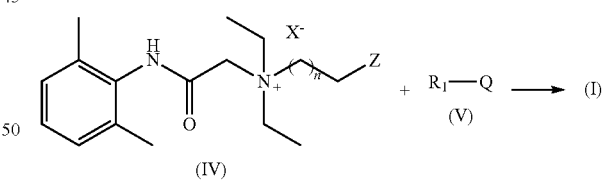

In the formula, X is selected from the group consisting of halogens and pharmaceutically acceptable anions, preferably bromine; $R_1$ is selected from the group consisting of straight chain or branch chain, substituted or unsubstituted, saturated or unsaturated $C_{2-30}$ alkyls and alkoxys; Q represents OH, COOH, or COCl; Z represents OH or OCOCl; n represents an integer selected from 1, 2, 3, and 4. Wherein, raw material (IV) can be prepared referring to those reported in publication No. CN103601650A.

Further investigation shows that in the presence of water or aqueous solvent, the above long-chain dimethylaniline derivative compounds with formula (I) structure can self-assemble into micelle or gel, and be further used in local anesthesia.

Wherein, said aqueous solvents are physiological saline or organic solvents including ethanol, 1,2-propylene glycol, glycerol, that can be miscible with water and allowed to be used in local injections. In the presence of water or aqueous solvent, said long-chain dimethylaniline derivative compounds of formula (I) according to the present invention, can become uniform stable hydrogels. Experiment shows when the concentration in water or aqueous solvent is high, said compounds may form gel state; when the concentration is low, they may form micelles.

Currently, micelle materials have already been more used in biomedical material field including gene therapy, et al. Experiment indicates that micelle textures, formed by self-assembly of long-chain dimethylaniline derivative compounds of formula (I) according to the present invention, are preferably used in local anesthetics.

Investigation shows that long-chain dimethylaniline derivative compounds of formula (I) according to the present invention can be used in the preparation of medicaments including local anesthetic, analgesic, and antipruritic agents, and/or the micelle textures or gels formed by their self-assembly can produce local anesthetic effects exceeding 72 hours, and thus have a favourable application perspective for the preparation of local anesthetics. In addition, said micelles or gels formed by self-assembly of above compounds can also be used as biocompatible adjuvants of a new type preparation and used in the preparation of biomaterials and/or carriers of medicinal package adjuvants or used in the delivery system. After packaging other medicaments, said micelles or gels can be further used as local anesthetic or analgesic medicaments, and used in the related medical therapy.

Based on the above, said compounds of formula (I) according to the present invention can further combine with general anesthetic medicaments including procaine, lidocaine, bupivacaine, and ropivacaine, and form medicaments with long-acting local anesthetic effects. Said micelles or gels formed by self-assembly of compounds of formula (I) according to the present invention can also further combine with active compounds of transient acceptor cation channel agonists including TRPV1 and/or TRPS, capsaicin, 4-hydroxy-3-methoxybenzyl nonanoate, eugenol and form local anesthetic medicaments.

Wherein, after compounds of formula (I) according to the present invention are used together with general anesthetic medicaments, the effective time reduces to 5 min, while the sense retardation time still keeps for 80 hours, but the motion retardation time greatly decreases and becomes 31~62 hours. Thus, motion-sensation isolation blocking is partly realized. This character makes the present invention possess a prospect being further used in clinical therapy. Postoperative patients are able to suitably exercise without pain, that is contributed to postoperative rehabilitation of patients. When compounds of formula (I) are used with capsaicin, 4-hydroxy-3-methoxybenzyl nonanoate and so on, the motion retardation time can be further reduced, and is only 11~20 hours. Thus, a bright application prospect can be expected.

Experimental results have shown that compounds of formula (I) and/or micelles or gels formed by self-assembly of said compounds can exert an in vivo elongated local anesthetic actions, and local anesthesia and/or analgesic activity can last more than 72 hours. In addition, the biomaterials can self-assemble into micelles or gels in water and have local anesthetic effect, as well as can further be used as the coating of medicinal bioactive molecules for treatment of pain, itching and the like and/or the drug carriers, together with as pharmaceutical adjuvants for delivery system. Thus, said materials have a favourable perspective.

Above contents of the present invention can further be illustrated by the specific embodiments of following examples. But it should not be understood that above subject scope of the present invention is limited to the following examples. Without department from above skills and spirits of the present invention, various substitutions or variations made according to the common technical knowledge and commonly-used means should be within the scope of the present invention.

SPECIFIC EMBODIMENTS

Example 1

Preparation of Intermediate (IV)

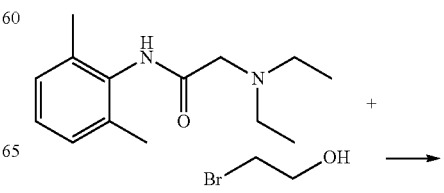

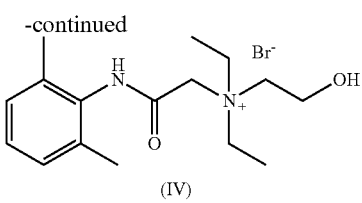

(IV)

Figure 1:
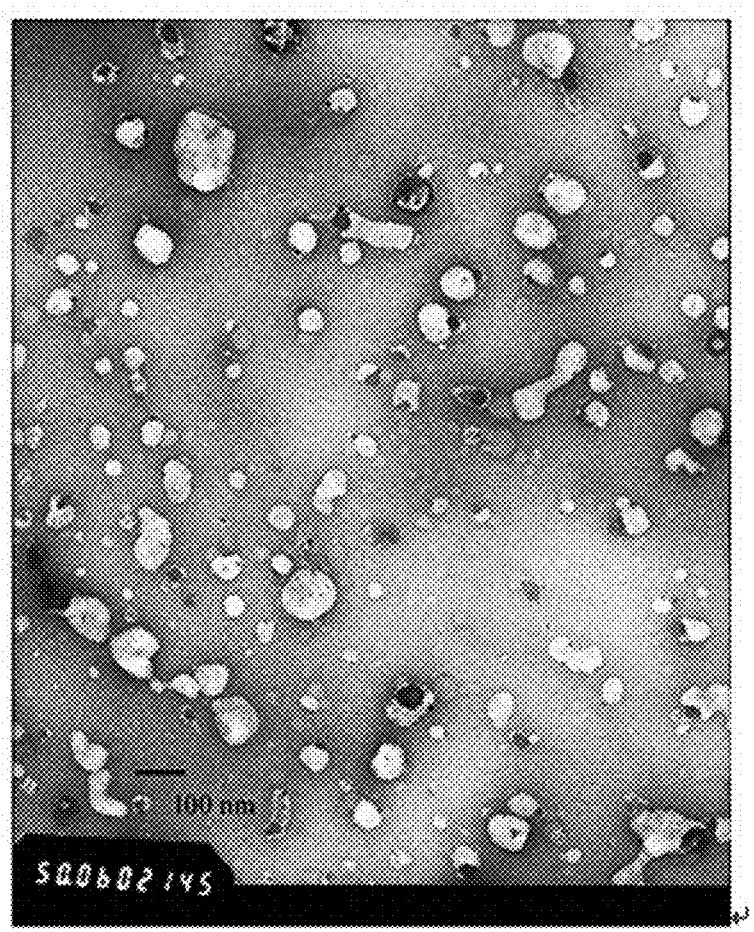
FIG. 1 Transmission electron microscopy image of formed micelle.

5 g N-diethylaminoacetyl-2,6-dimethylaniline was dissolved in 50 ml 2-bromoethanol, and in well-closed container, allowed to react at 90° C. for 24 h. After that, the reaction solution was slowly dropped to 200 ml absolute ethyl ether under stirring. White solids precipitated, that was filtered and dried, to provide the product (IV) (2.37 g, yield 31%).

Example 2

Preparation of Intermediate (IV)

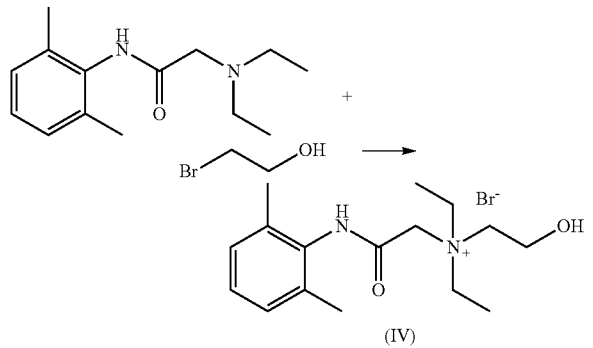

(IV)

4.5 g N-diethylaminoacetyl-2,6-dimethylaniline and 2.4 g 2-bromoethanol were uniformly dissolved in 30 ml 1,2-dichloroethane, and in well-closed tube, allowed to react at 100° C. After that, the reaction solution was slowly dropped to 200 ml absolute ethyl ether under stirring. White solids precipitated, that was filtered and dried, to provide the product (IV) (2.06 g, yield 30%).

$^1$H NMR (400 MHz, CD$_3$OD) δ: 7.11~7.16 (m, 3H), 4.50~4.51 (m, 2H), 4.05~4.07 (m, 2H), 3.75~3.87 (m, 6H), 2.26 (s, 6H), 1.43 (t, J=7.2 Hz, 6H).

$^{13}$C NMR (100 MHz, CD$_3$OD) δ: 8.28, 18.65, 56.81, 56.93, 58.48, 61.63, 128.92, 129.31, 134.19, 136.80, 164.15.

HRMS: [C$_{16}$H$_{27}$N$_2$O$_2$]$^+$, 279.2075.

Example 3

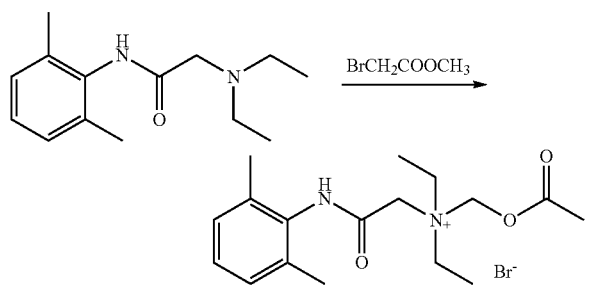

3.0 g N-diethylaminoacetyl-2,6-dimethylaniline and equivalent methyl 2-bromoacetate were uniformly dissolved in 30 ml 1,2-dichloroethane, and in well-closed tube, allowed to react at 100° C. for 6 h. After that, the reaction solution was slowly dropped to 200 ml absolute ethyl ether under stirring. White solids precipitated, that was filtered and dried, to provide the product (IV) (1.96 g, yield 40%).

$^1$H NMR (400 MHz, CDCl$_3$) δ: 7.11~7.16 (m, 3H), 6.03~6.07 (m, 2H), 4.15~4.21 (m, 2H), 3.75~3.87 (m, 6H), 2.26 (s, 3H), 2.15 (s, 6H), 1.25 (t, J=7.2 Hz, 6H).

$^{13}$C NMR (100 MHz, CDCl$_3$) δ: 8.28, 18.65, 20.4, 56.81, 56.93, 58.48, 61.63, 128.92, 129.31, 134.19, 136.80, 164.15, 170.2.

HRMS: [C$_{17}$H$_{27}$N$_2$O$_3$]$^+$, 307.4135.

Example 4

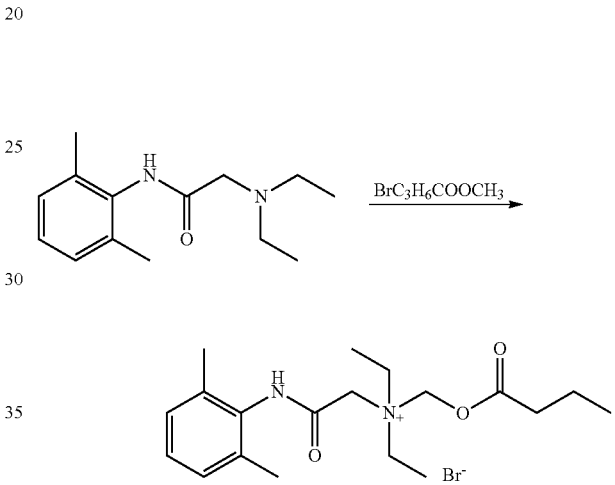

Synthetic procedures are same as Example 3, with a yield of 36%.

$^1$H NMR (400 MHz, CDCl$_3$) δ: 7.11~7.16 (m, 3H), 6.03~6.07 (m, 2H), 4.15~4.21 (m, 2H), 3.75~3.87 (m, 6H), 2.35 (t, J=6.8 Hz, 2H), 2.26 (s, 6H), 2.12 (s, 6H), 1.79 (m, 2H), 1.25 (t, J=7.2 Hz, 6H), 0.90 (t, J=7.0 Hz, 3H).

$^{13}$C NMR (100 MHz, CDCl$_3$) δ: 7.32, 13.50, 18.40, 18.65, 35.82, 56.81, 56.93, 58.48, 61.63, 128.92, 129.31, 134.19, 136.80, 164.15, 170.2.

HRMS: [C$_{19}$H$_{31}$N$_2$O$_3$]$^+$, 335.4625.

Example 5

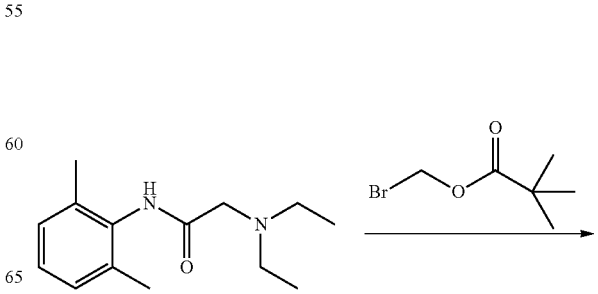

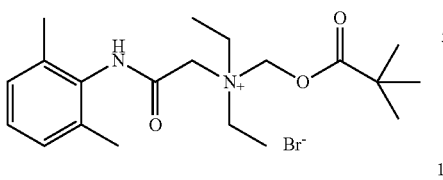

Synthetic procedures are same as Example 3, with a yield of 32%.

$^1$H NMR (400 MHz, CDCl$_3$) δ: 7.11~7.16 (m, 3H), 6.03~6.07 (m, 2H), 4.15~4.21 (m, 2H), 3.75~3.87 (m, 6H), 2.26 (s, 6H), 2.12 (s, 6H), 1.25 (t, J=7.2 Hz, 6H), 1.28 (s, 9H).

$^{13}$C NMR (100 MHz, CDCl$_3$) δ: 7.32, 18.65, 27.43, 38.42, 56.81, 56.93, 58.48, 61.63, 128.92, 129.31, 134.19, 136.80, 164.15, 170.2.

HRMS: [C$_{20}$H$_{33}$N$_2$O$_3$]$^+$, 349.4895.

Example 6

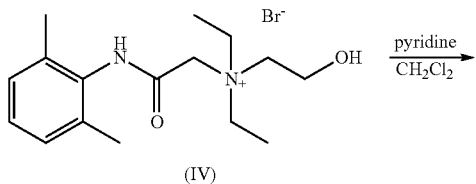

To 100 ml round bottom flask, were added 3 g compound (IV), 50 ml dichloromethane, 0.7 g pyridine, and then uniformly mixed at room temperature, to which the solution of 0.7 g acetyl chloride in 10 ml dichloromethane was added dropwise. The mixture was stirred at room temperature for 6 h. The reaction solution was concentrated to dryness under reduced pressure, then subjected to silica gel column chromatography eluting with dichloromethane:methanol (20:1), to obtain white powder solid (1.06 g, yield 32%). Detection results:

$^1$H NMR (400 MHz, CDCl$_3$) δ: 10.36 (s, 1H), 7.03~7.11 (m, 3H), 4.99 (br, 2H), 4.61 (t, J=4.8 Hz, 2H), 4.01 (t, J=4.9 Hz, 2H), 3.68~3.77 (m, 4H), 2.26 (br, 6H), 2.10 (br, 3H), 1.49 (t, J=7.2 Hz, 3H).

$^{13}$C NMR (100 MHz, CDCl$_3$) δ: 8.47, 18.92, 20.87, 56.43, 57.48, 57.77, 57.82, 127.61, 128.19, 132.84, 135.10, 161.80, 170.03.

HRMS: [C$_{18}$H$_{29}$N$_2$O$_3$]$^+$, 321.2177.

Example 7

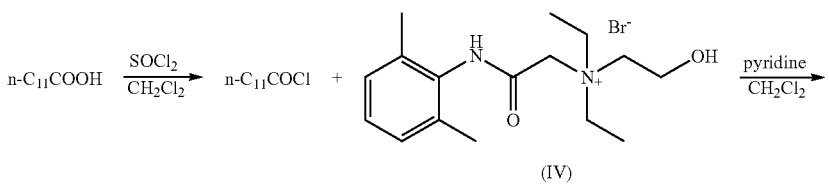

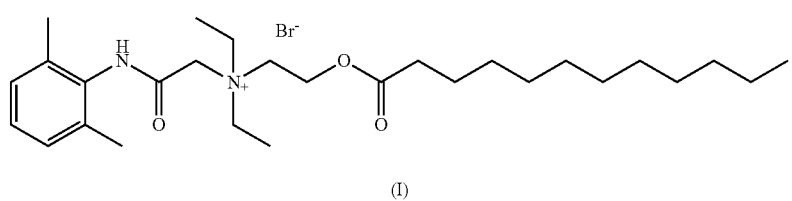

To 100 ml round bottom flask, were added 1.7 g dodecanoic acid (IV), 20 ml dichloromethane, 2 ml sulfoxide chloride, and then stirred under reflux for 1 h. The mixture was concentrated to dryness under reduced pressure. The residue was dissolved in 20 ml dichloromethane and kept for use.

To another 100 ml round bottom flask, were added 3.0 g compound (IV), 0.7 g pyridine, and then uniformly mixed at room temperature, to which the solution of said residue in 20 ml dichloromethane was slowly dropped and stirred at room temperature for 12 h.

The reaction solution was concentrated to dryness, and then subjected to silica gel column chromatography eluting with dichloromethane:methanol (20:1~5:1), to obtain white powder solid (1.58 g, yield 35%). Detection results:

$^1$H NMR (400 MHz, CDCl$_3$) δ: 10.43 (br, 1H), 7.03~7.11 (m, 3H), 5.06 (br, 2H), 4.61~4.63 (m, 2H), 4.00~4.02 (m, 2H), 3.71~3.77 (m, 2H), 2.34 (t, J=7.4 Hz, 2H), 2.77 (br, 6H), 1.59 (t, J=7.0 Hz, 2H), 1.52 (t, J=7.0 Hz, 2H), 1.26 (br, 16H), 0.88 (t, J=6.5 Hz, 3H).

$^{13}$C NMR (100 MHz, CDCl$_3$) δ: 8.51, 14.11, 18.90, 18.93, 22.67, 24.61, 26.90, 29.08, 29.22, 29.32, 29.43, 29.58, 31.89, 33.95, 56.45, 57.18, 57.77, 127.60, 128.19, 132.82, 135.08, 161.81, 172.90.

HRMS: $[C_{28}H_{49}N_2O_3]^+$, 461.3734.

Example 8

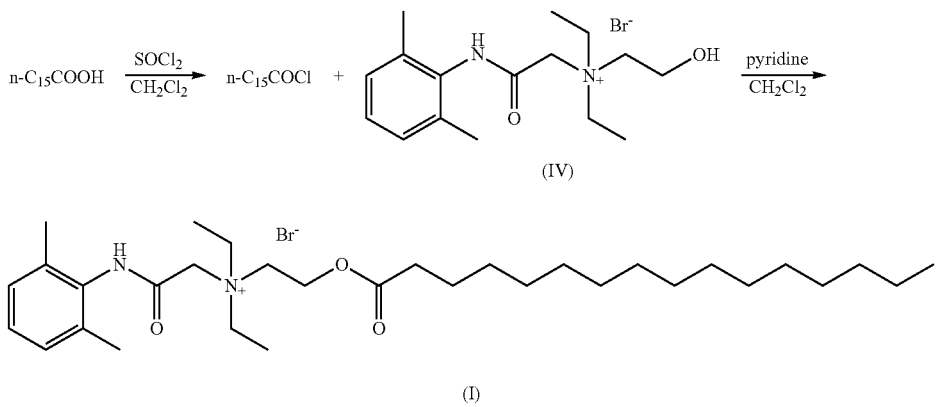

(IV)

(I)

Referring to the method of example 7, 1.54 g white powder solid was obtained, with a yield of 31%.

$^1$H NMR (400 MHz, CDCl$_3$) δ: 10.48 (s, 1H), 7.04~7.11 (m, 3H), 5.13 (s, 2H), 4.64 (t, J=5.2 Hz, 2H), 3.98 (t, J=5.2 Hz, 2H), 3.68~3.79 (m, 4H), 2.35 (t, J=7.6 Hz, 2H), 2.28 (br, 6H), 1.61~1.73 (m, 2H), 1.57 (t, J=7.2 Hz, 2H), 1.26 (br, 24H), 0.88 (t, J=7.0 Hz, 3H).

$^{13}$C NMR (100 MHz, CDCl$_3$) δ: 8.52, 14.13, 18.97, 22.70, 24.62, 29.90, 29.23, 29.36, 29.44, 29.60, 29.66, 29.69, 31.92, 33.95, 56.49, 57.06, 57.87, 127.67, 128.23, 132.73, 135.01, 161.63, 172.89.

HRMS: $[C_{32}H_{57}N_2O_3]^+$, 517.4368.

Example 9

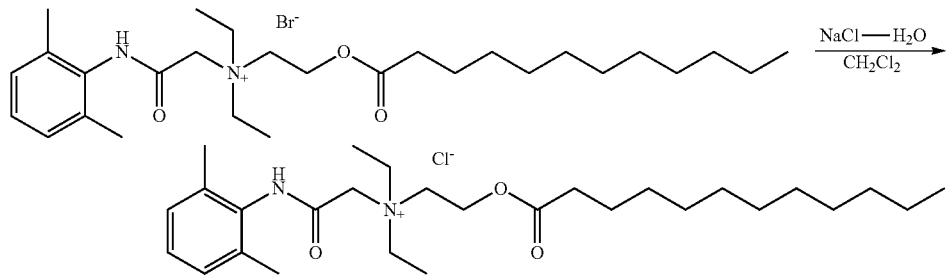

1.0 g product obtained in example 7 was dissolved in 20 ml dichloromethane, and extracted with saturated sodium chloride aqueous solution (20 ml×5) and separated. The organic layer was concentrated to dryness, and then subjected to silica gel column chromatography eluting with dichloromethane:methanol (20:1~5:1), to obtain white powder solid (0.98 g, yield 90%). Detection results:

$^1$H NMR (400 MHz, CDCl$_3$) δ: 10.43 (br, 1H), 7.03~7.11 (m, 3H), 5.06 (br, 2H), 4.61~4.63 (m, 2H), 4.00~4.02 (m, 2H), 3.71~3.77 (m, 2H), 2.34 (t, J=7.4 Hz, 2H), 2.77 (br, 6H), 1.59 (t, J=7.0 Hz, 2H), 1.52 (t, J=7.0 Hz, 2H), 1.26 (br, 16H), 0.88 (t, J=6.5 Hz, 3H).

By detection with chromatography of ions, the content of chloridion was 99.9%.

Example 10

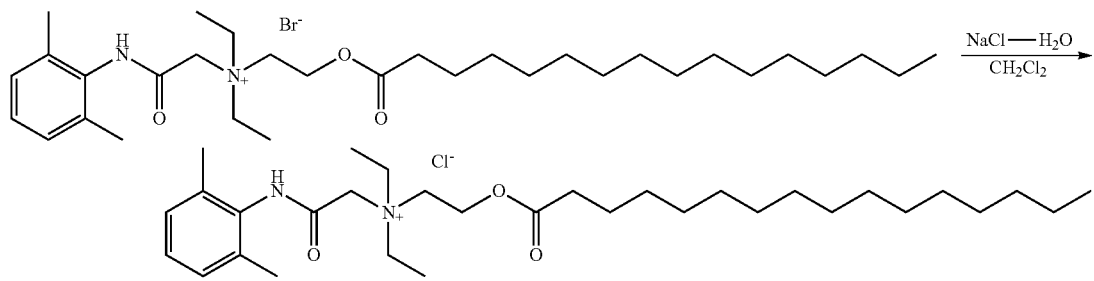

1.0 g product obtained in example 8 was dissolved in 20 ml dichloromethane, and extracted with saturated sodium chloride aqueous solution (20 ml×5), then separated. The organic layer was concentrated to dryness, and then subjected to silica gel column chromatography eluting with dichloromethane:methanol (20:1~5:1), to obtain white powder solid (0.98 g, yield 91%). Detection results:

$^1$H NMR (400 MHz, CDCl$_3$) δ: 10.48 (s, 1H), 7.04~7.11 (m, 3H), 5.13 (s, 2H), 4.64 (t, J=5.2 Hz, 2H), 3.98 (t, J=5.2 Hz, 2H), 3.68~3.79 (m, 4H), 2.35 (t, J=7.6 Hz, 2H), 2.28 (br, 6H), 1.61~1.73 (m, 2H), 1.57 (t, J=7.2 Hz, 2H), 1.26 (br, 24H), 0.88 (t, J=7.0 Hz, 3H).

By detection with chromatography of ions, the content of chloridion was 99.9%.

Example 11

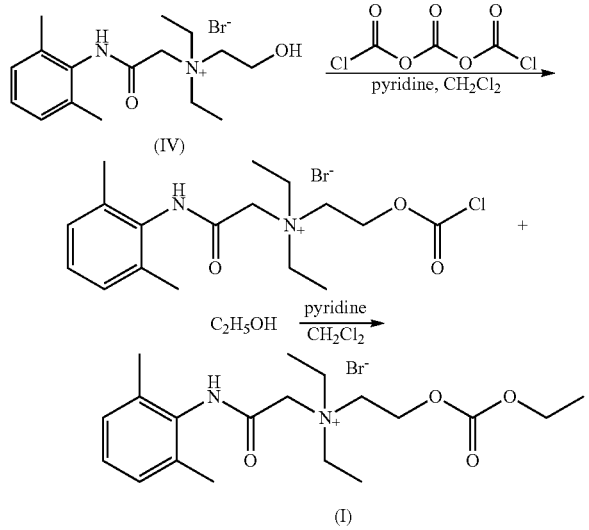

To 100 ml round bottom flask, were added 3.0 g compound (IV), 0.84 g triphosgene, 30 ml dichloromethane, and then uniformly mixed at room temperature. 0.6 g Pyridine was slowly dropped to the obtained mixture, and stirred for 2 h at room temperature.

The solution of 2.0 g ethanol in 40 ml dichloromethane was added dropwise. The mixture was then stirred at room temperature for 12 h.

The reaction solution was concentrated to dryness under reduced pressure, then subjected to silica gel column chromatography eluting with dichloromethane:methanol (20:1~5:1), to obtain white powder solid (1.55 g, yield 43%). Detection results:

$^1$H NMR (400 MHz, CDCl$_3$) δ: 10.48 (s, 1H), 7.04~7.11 (m, 3H), 5.05 (br, 2H), 4.68 (br, 2H), 4.22 (t, J=7.1 Hz, 2H), 4.06 (br, 2H), 3.74 (br, 2H), 2.27 (br, 6H), 1.52 (br, 6H), 1.30 (t, J=7.1 Hz, 3H).

$^{13}$C NMR (100 MHz, CDCl$_3$) δ: 8.52, 14.16, 18.90, 56.59, 57.88, 60.64, 65.08, 127.57, 128.17, 132.88, 135.12, 154.15, 161.79.

HRMS: [C$_{19}$H$_{31}$N$_2$O$_4$]$^+$, 351.2650.

Example 12

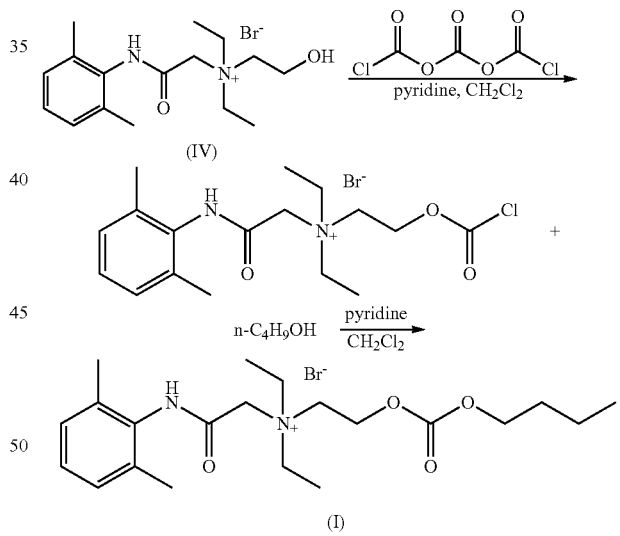

To 100 ml round bottom flask, were added 3.0 g compound (IV), 0.84 g triphosgene, 30 ml dichloromethane, and then uniformly mixed at room temperature. 0.6 g Pyridine was slowly dropped to the obtained mixture, and stirred for 2 h at room temperature.

The solution of 2.0 g n-butanol in 40 ml dichloromethane was added dropwise. The mixture was then stirred at room temperature for 12 h.

The reaction solution was concentrated to dryness under reduced pressure, then subjected to silica gel column chromatography eluting with dichloromethane:methanol (20: 1~5:1), to obtain white powder solid (1.30 g, yield 35%).

Detection results:

$^1$H NMR (400 MHz, CDCl$_3$) δ: 11.04 (s, 1H), 7.02~7.10 (m, 3H), 5.05 (br, 2H), 4.68 (br, 2H), 4.14 (t, J=6.8 Hz, 2H), 4.04 (br, 2H), 3.66~3.77 (m, 4H), 2.27 (s, 6H), 1.66 (m, 2H), 1.52 (t, J=6.8 Hz, 6H), 1.30 (t, J=7.2 Hz, 3H).

$^{13}$C NMR (100 MHz, CDCl$_3$) δ: 8.34, 13.62, 18.84, 30.47, 56.43, 57.58, 57.84, 60.59, 68.90 76.77, 127.42, 128.12, 133.11, 135.01, 154.31, 161.75.

HRMS: [C$_{21}$H$_{35}$N$_2$O$_4$]$^+$, 379.2601.

Example 13

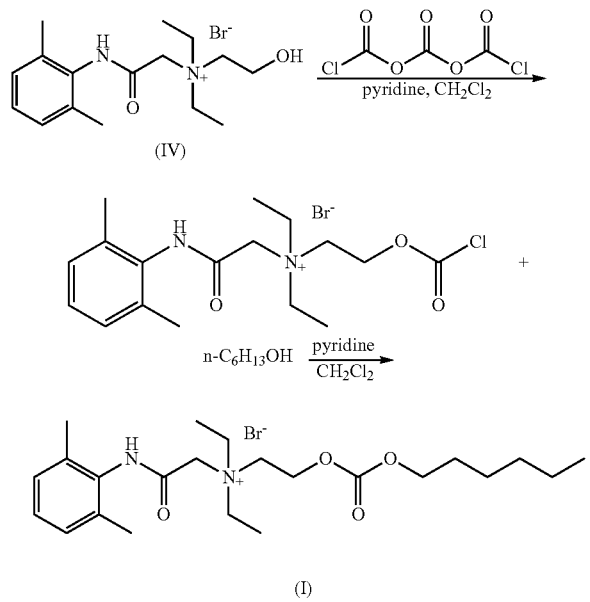

To 100 ml round bottom flask, were added 3.0 g compound (IV), 0.84 g triphosgene, 30 ml dichloromethane, and then uniformly mixed at room temperature. 0.6 g Pyridine was slowly dropped to the obtained mixture, and stirred for 2 h at room temperature.

The solution of 2.0 g n-hexanol in 40 ml dichloromethane was added dropwise. The mixture was then stirred at room temperature for 12 h.

The reaction solution was evaporated under reduced pressure, then subjected to silica gel column chromatography eluting with dichloromethane:methanol (20:1~5:1), to obtain white powder solid (1.30 g, yield 34%). Detection results:

$^1$H NMR (400 MHz, CDCl$_3$) δ: 10.89 (s, 1H), 7.03~7.10 (m, 3H), 5.07 (br, 2H), 4.68 (br, 2H), 4.16 (t, J=6.8 Hz, 2H), 4.04 (m, 2H), 3.67~3.80 (m, 4H), 2.28 (s, 6H), 1.66 (m, 2H), 1.54 (t, J=6.8 Hz, 6H), 1.31 (t, J=7.2 Hz, 3H).

$^{13}$C NMR (100 MHz, CDCl$_3$) δ: 8.42, 14.00, 14.21, 18.89, 22.49, 25.26, 28.45, 31.32, 56.54, 57.71, 57.88, 60.42, 60.53, 69.33, 76.73, 127.52, 128.17, 132.96, 135.02, 154.31, 161.71.

HRMS: [C$_{23}$H$_{39}$N$_2$O$_4$]$^+$, 407.3347.

Example 14

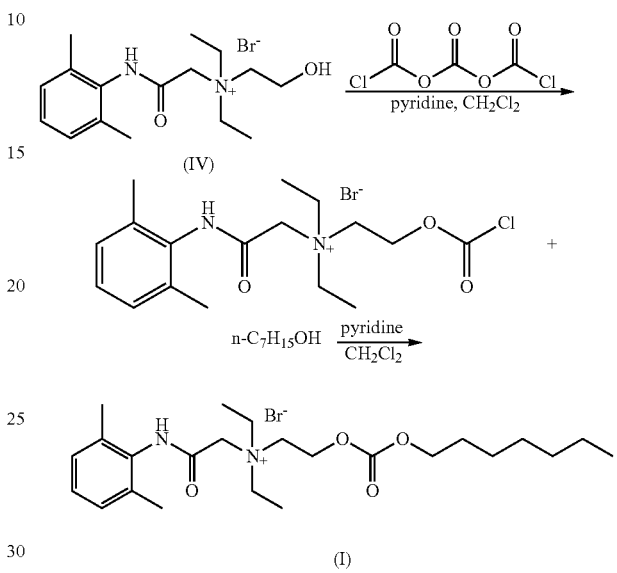

To 100 ml round bottom flask, were added 3.0 g compound (IV), 0.84 g triphosgene, 30 ml dichloromethane, and then uniformly mixed at room temperature. 0.6 g Pyridine was slowly dropped to the obtained mixture, and stirred for 2 h at room temperature.

The solution of 2.0 g n-heptanol in 40 ml dichloromethane was added dropwise. The mixture was then stirred at room temperature for 12 h.

The reaction solution was concentrated to dryness under reduced pressure, then subjected to silica gel column chromatography eluting with dichloromethane:methanol (20:1~5:1), to obtain white powder solid (1.30 g, yield 34%). Detection results:

$^1$H NMR (400 MHz, CDCl$_3$) δ: 10.34 (s, 1H), 7.00~7.08 (m, 3H), 5.00 (m, 2H), 4.64 (br, 2H), 4.16 (t, J=6.8 Hz, 2H), 4.04 (m, 2H), 3.66~3.76 (m, 4H), 2.24 (s, 6H), 1.60~1.63 (m, 2H), 1.54~1.56 (m, 8H), 0.86 (t, J=7.2 Hz, 3H).

$^{13}$C NMR (100 MHz, CDCl$_3$) δ: 8.33, 14.06, 14.19, 18.82, 21.06, 22.54, 25.53, 26.89, 28.48, 28.81, 31.64, 56.40, 57.56, 57.82, 60.39, 60.59, 69.33, 76.79, 127.42, 128.12, 133.11, 135.04, 154.31, 161.77.

HRMS: [C$_{24}$H$_{41}$N$_2$O$_4$]$^+$, 421.3070.

Example 15

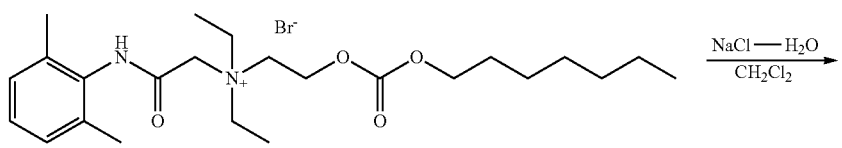

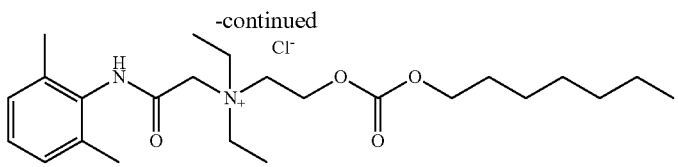

1.0 g product obtained in example 14 was dissolved in 20 ml dichloromethane, and extracted with saturated aqueous sodium chloride solution (20 ml×5) and separated. The organic layer was concentrated to dryness, and then subjected to silica gel column chromatography eluting with dichloromethane:methanol (20:1~5:1), to obtain white powder solid (1.0 g, yield 92%). Detection results:

$^1$H NMR (400 MHz, CDCl$_3$) δ: 10.34 (s, 1H), 7.00~7.08 (m, 3H), 5.00 (m, 2H), 4.64 (br, 2H), 4.16 (t, J=6.8 Hz, 2H), 4.04 (m, 2H), 3.66~3.76 (m, 4H), 2.24 (s, 6H), 1.60~1.63 (m, 2H), 1.54~1.56 (m, 8H), 0.86 (t, J=7.2 Hz, 3H).

By detection with chromatography of ions, the content of chloridion was more than 99.9%.

Example 16

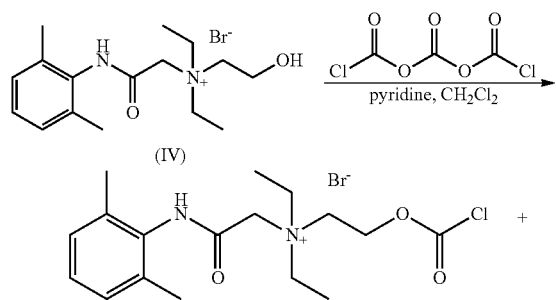

then uniformly mixed at room temperature. 0.6 g Pyridine was slowly dropped to the obtained mixture, and stirred for 2 h at room temperature.

The solution of 2.0 g n-octyl alcohol in 40 ml dichloromethane was added dropwise. The mixture was then stirred at room temperature for 12 h.

The reaction solution was evaporated under reduced pressure, then subjected to silica gel column chromatography eluting with dichloromethane:methanol (20:1~5:1), to obtain white powder solid (1.30 g, yield 35%). Detection results:

$^1$H NMR (400 MHz, CDCl$_3$) δ: 11.04 (s, 1H), 7.02~7.10 (m, 3H), 5.05 (m, 2H), 4.68 (br, 2H), 4.16 (t, J=6.8 Hz, 2H), 4.04 (m, 2H), 3.66~3.76 (m, 4H), 2.27 (s, 6H), 1.65~1.69 (m, 2H), 1.52 (t, J=5.4 Hz, 6H), 1.24~1.31 (m, 10H), 0.89 (t, J=7.2 Hz, 3H).

$^{13}$C NMR (100 MHz, CDCl$_3$) δ: 8.49, 14.09, 14.19, 18.92, 22.62, 25.58, 28.48, 29.12, 31.74, 56.54, 57.81, 60.59, 69.24, 76.77, 127.57, 128.16, 132.87, 135.13, 154.29, 161.78.

HRMS: [C$_{25}$H$_{43}$N$_2$O$_4$]$^+$, 435.3223.

Example 17

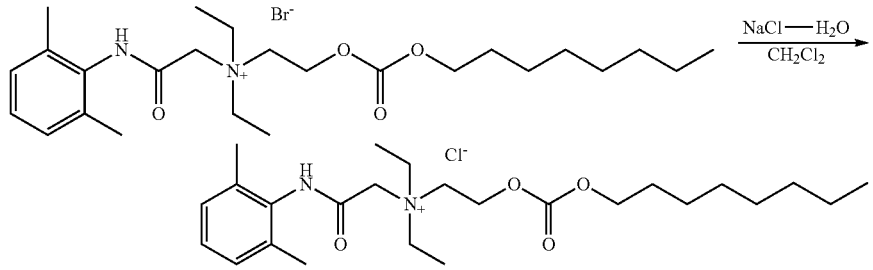

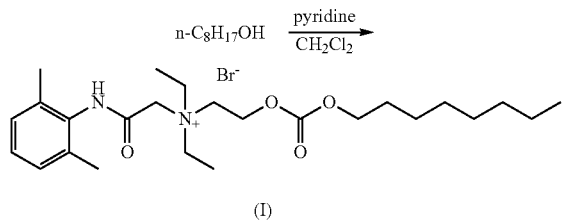

To 100 ml round bottom flask, were added 3.0 g compound (IV), 0.84 g triphosgene, 30 ml dichloromethane, and 1.0 g product obtained in example 16 was dissolved in 20 ml dichloromethane, and extracted with saturated aqueous sodium chloride solution (20 ml×5) and separated. The organic layer was concentrated to dryness, and then subjected to silica gel column chromatography eluting with dichloromethane:methanol (20:1~5:1), to obtain white powder solid (1.0 g, yield 92%). Detection results:

$^1$H NMR (400 MHz, CDCl$_3$) δ: 11.04 (s, 1H), 7.02~7.10 (m, 3H), 5.05 (m, 2H), 4.68 (br, 2H), 4.16 (t, J=6.8 Hz, 2H), 4.04 (m, 2H), 3.66~3.76 (m, 4H), 2.27 (s, 6H), 1.65~1.69 (m, 2H), 1.52 (t, J=5.4 Hz, 6H), 1.24~1.31 (m, 10H), 0.89 (t, J=7.2 Hz, 3H).

By detection with chromatography of ions, the content of chloridion was more than 99.9%.

Example 18

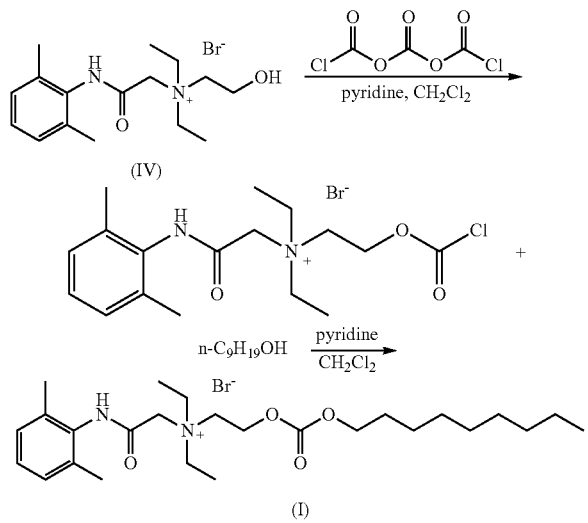

To 100 ml round bottom flask, were added 3.0 g compound (IV), 0.84 g triphosgene, 30 ml dichloromethane, and then uniformly mixed at room temperature. 0.6 g Pyridine was slowly dropped to the obtained mixture, and stirred for 2 h at room temperature.

The solution of 1.2 g n-nonyl alcohol in 40 ml dichloromethane was added dropwise. The mixture was then stirred at room temperature for 12 h.

The reaction solution was concentrated to dryness under reduced pressure, then subjected to silica gel column chromatography eluting with dichloromethane:methanol (20:1~5:1), to obtain white powder solid (1.73 g, yield 39%).

Detection results:

$^1$H NMR (400 MHz, CDCl$_3$) δ: 10.47 (br, 1H), 7.03~7.11 (m, 3H), 5.08 (s, 2H), 4.66~4.69 (m, 2H), 4.15 (t, J=6.7 Hz, 2H), 4.04~4.11 (m, 2H), 3.67~3.83 (m, 4H), 2.28 (br, 6H), 1.99 (br, 2H), 1.63-1.70 (m, 2H), 1.54 (t, J=7.2 Hz, 6H), 1.30~1.37 (m, 4H), 0.90 (t, J=4.0 Hz, 3H).

$^{13}$C NMR (100 MHz, CDCl$_3$) δ: 8.50, 13.92, 18.92, 18.94, 22.24, 27.69, 28.18, 56.57, 57.85, 60.54, 69.30, 127.62, 128.19, 132.80, 135.11, 154.30, 161.75.

HRMS: [C$_{26}$H$_{45}$N$_2$O$_4$]$^+$, 449.3387.

Example 19

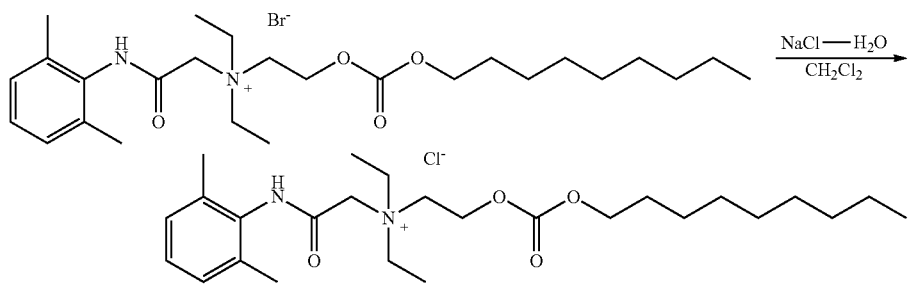

1.0 g product obtained in example 18 was dissolved in 20 ml dichloromethane, and extracted with saturated aqueous sodium chloride solution (20 ml×5) and separated. The organic layer was concentrated to dryness, and then subjected to silica gel column chromatography eluting with dichloromethane:methanol (20:1~5:1), to obtain white powder solid (1.0 g, yield 92%).

$^1$H NMR (400 MHz, CDCl$_3$) δ: 10.47 (br, 1H), 7.03~7.11 (m, 3H), 5.08 (s, 2H), 4.66~4.69 (m, 2H), 4.15 (t, J=6.7 Hz, 2H), 4.04~4.11 (m, 2H), 3.67~3.83 (m, 4H), 2.28 (br, 6H), 1.99 (br, 2H), 1.63-1.70 (m, 2H), 1.54 (t, J=7.2 Hz, 6H), 1.30~1.37 (m, 4H), 0.90 (t, J=4.0 Hz, 3H).

By detection with chromatography of ions, the content of chloridion was more than 99.9%.

Example 20

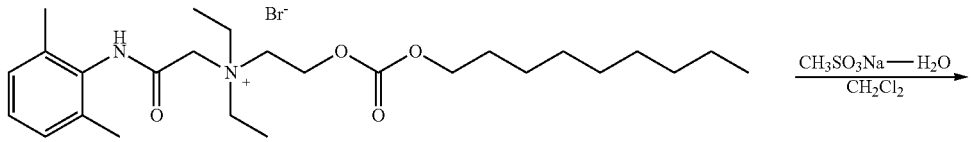

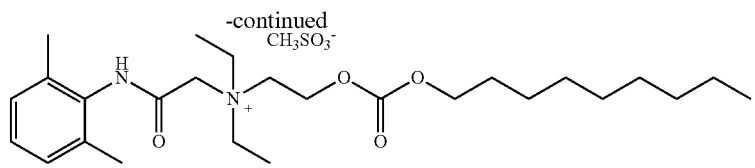

1.0 g product obtained in example 18 was dissolved in 20 ml dichloromethane, and extracted with saturated aqueous sodium mesilate solution (20 ml×5) and separated. The organic layer was concentrated to dryness, and then subjected to silica gel column chromatography eluting with dichloromethane:methanol (20:1~5:1), to obtain white powder solid (1.0 g, yield 92%).

$^1$H NMR (400 MHz, CDCl$_3$) δ: 10.47 (br, 1H), 7.03~7.11 (m, 3H), 5.08 (s, 2H), 4.66~4.69 (m, 2H), 4.15 (t, J=6.7 Hz, 2H), 4.04~4.11 (m, 2H), 3.67~3.83 (m, 4H), 2.28 (br, 6H), 1.99 (br, 2H), 1.63~1.70 (m, 2H), 1.54 (t, J=7.2 Hz, 6H), 1.30~1.37 (m, 4H), 0.90 (t, J=4.0 Hz, 3H).

By detection with chromatography of ions, the content of mesilate anions was more than 99.9%.

Example 21

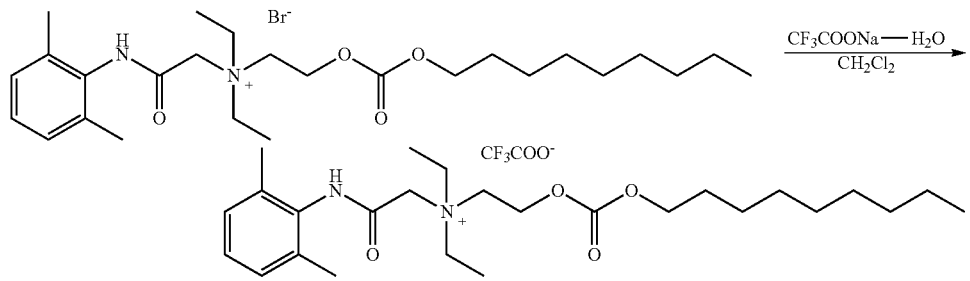

1.0 g product obtained in example 18 was dissolved in 20 ml dichloromethane, and extracted with saturated aqueous sodium trifluoroacetate solution (20 ml×5) and separated. The organic layer was concentrated to dryness, and then subjected to silica gel column chromatography eluting with dichloromethane:methanol (20:1~5:1), to obtain white powder solid (1.0 g, yield 92%).

$^1$H NMR (400 MHz, CDCl$_3$) δ: 10.47 (br, 1H), 7.03~7.11 (m, 3H), 5.08 (s, 2H), 4.66~4.69 (m, 2H), 4.15 (t, J=6.7 Hz, 2H), 4.04~4.11 (m, 2H), 3.67~3.83 (m, 4H), 2.28 (br, 6H), 1.99 (br, 2H), 1.63-1.70 (m, 2H), 1.54 (t, J=7.2 Hz, 6H), 1.30~1.37 (m, 4H), 0.90 (t, J=4.0 Hz, 3H).

By detection with chromatography of ions, the content of trifluoroacetate anions was more than 99.9%.

Example 22

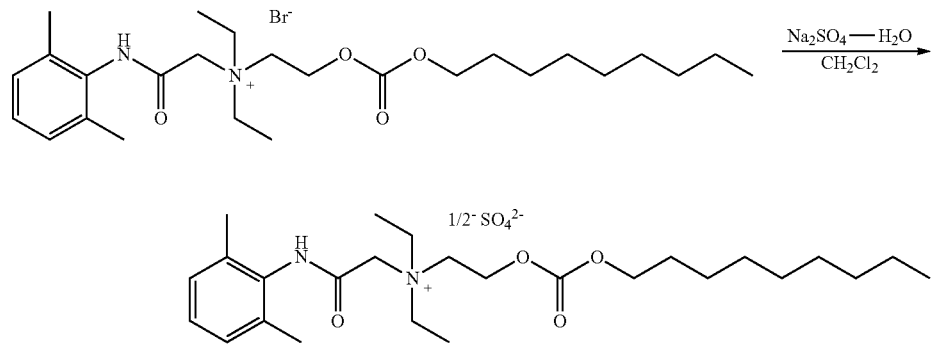

1.0 g product obtained in example 18 was dissolved in 20 ml dichloromethane, and extracted with saturated aqueous sodium sulfate solution (20 ml×5) and separated. The organic layer was concentrated to dryness, and then subjected to silica gel column chromatography eluting with dichloromethane:methanol (20:1~5:1), to obtain white powder solid (1.0 g, yield 92%).

$^1$H NMR (400 MHz, CDCl$_3$) δ: 10.47 (br, 1H), 7.03~7.11 (m, 3H), 5.08 (s, 2H), 4.66~4.69 (m, 2H), 4.15 (t, J=6.7 Hz, 2H), 4.04~4.11 (m, 2H), 3.67~3.83 (m, 4H), 2.28 (br, 6H), 1.99 (br, 2H), 1.63-1.70 (m, 2H), 1.54 (t, J=7.2 Hz, 6H), 1.30~1.37 (m, 4H), 0.90 (t, J=4.0 Hz, 3H).

By detection with chromatography of ions, the content of sulfate anions was more than 99.9%.

Example 23

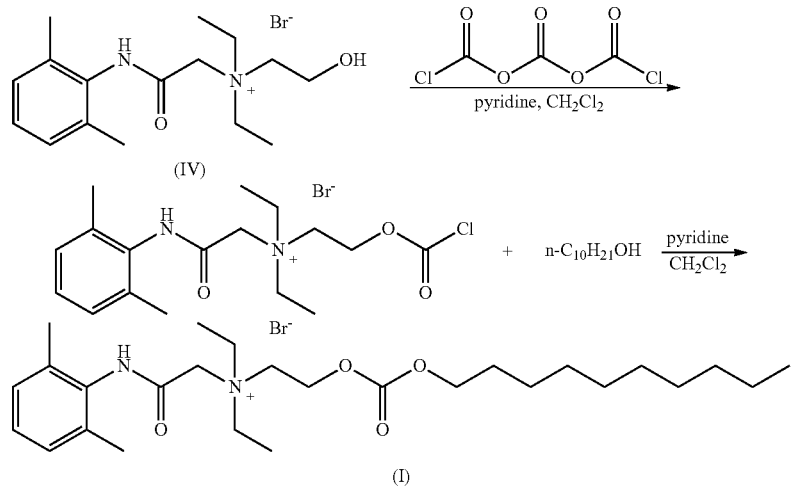

Referring to the method of Example 18, white powder solid was obtained, with a yield of 40%.

$^1$H NMR (400 MHz, CDCl$_3$) δ: 10.58 (br, 1H), 7.02~7.10 (m, 3H), 5.07 (s, 2H), 4.66~4.69 (m, 2H), 4.15 (t, J=6.8 Hz, 2H), 4.04~4.07 (m, 2H), 3.68~3.79 (m, 4H), 2.27 (br, 6H), 1.65 (t, J=7.1 Hz, 2H), 1.53 (t, J=7.2 Hz, 6H), 1.27~1.30 (m, 14H), 0.88 (t, J=6.6 Hz, 3H).

$^{13}$C NMR (100 MHz, CDCl$_3$) δ: 8.49, 14.13, 18.92, 22.68, 25.60, 28.50, 29.18, 29.30, 29.48, 29.52, 31.88, 56.56, 57.81, 57.89, 60.56, 69.29, 127.57, 128.18, 132.87, 135.10, 154.30, 161.75.

HRMS: [C$_{27}$H$_{47}$N$_2$O$_4$]$^+$, 463.3553.

Example 24

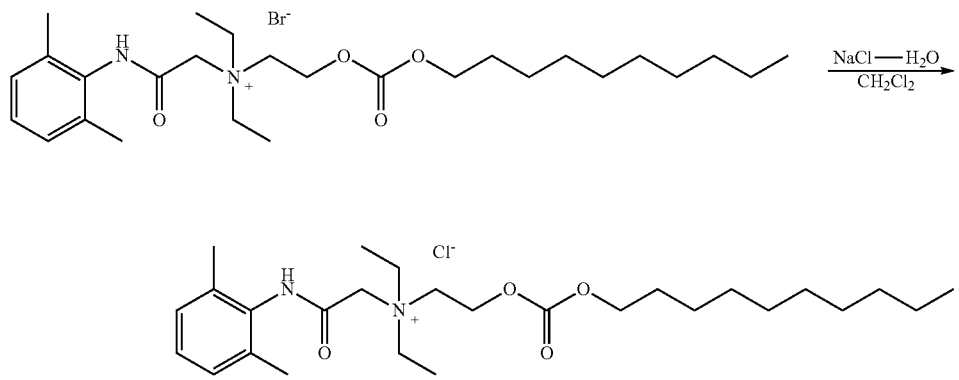

1.0 g product obtained in example 23 was dissolved in 20 ml dichloromethane, and extracted with saturated aqueous sodium chloride solution (20 ml×5) and separated. The organic layer was concentrated to dryness, and then subjected to silica gel column chromatography eluting with dichloromethane:methanol (20:1~5:1), to obtain white powder solid (1.0 g, yield 92%).

$^1$H NMR (400 MHz, CDCl$_3$) δ: 10.58 (br, 1H), 7.02~7.10 (m, 3H), 5.07 (s, 2H), 4.66~4.69 (m, 2H), 4.15 (t, J=6.8 Hz, 2H), 4.04~4.07 (m, 2H), 3.68~3.79 (m, 4H), 2.27 (br, 6H), 1.65 (t, J=7.1 Hz, 2H), 1.53 (t, J=7.2 Hz, 6H), 1.27~1.30 (m, 14H), 0.88 (t, J=6.6 Hz, 3H).

By detection with chromatography of ions, the content of chloridions was more than 99.9%.

Example 25

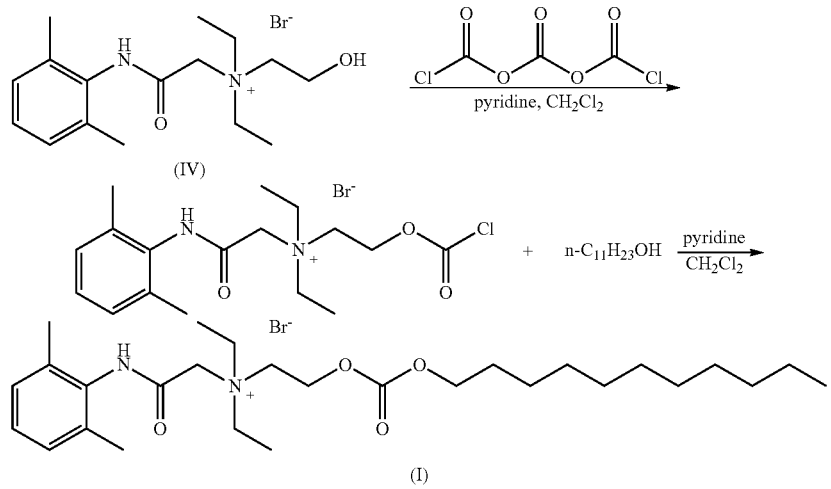

Referring to the method of Example 18, white powder solid was obtained, with a yield of 42%.

$^1$H NMR (400 MHz, CDCl$_3$) δ: 10.54 (br, 1H), 7.03~7.11 (m, 3H), 5.08 (s, 2H), 4.66~4.69 (m, 2H), 4.15 (t, J=6.8 Hz, 2H), 4.04~4.06 (m, 2H), 3.68~3.80 (m, 4H), 2.28 (br, 6H), 1.96 (br, 1H), 1.65 (t, J=7.1 Hz, 2H), 1.54 (t, J=7.2 Hz, 6H), 1.26~1.30 (m, 16H), 0.88 (t, J=6.6 Hz, 3H).

$^{13}$C NMR (100 MHz, CDCl$_3$) δ: 8.48, 14.13, 18.91, 22.68, 25.59, 28.50, 29.18, 29.32, 29.48, 29.57, 29.59, 31.90, 56.57, 57.82, 57.87, 60.52, 69.34, 127.60, 128.18, 132.82, 135.09, 154.30, 161.74.

HRMS: [C$_{28}$H$_{49}$N$_2$O$_4$]$^+$, 477.3694.

Example 26

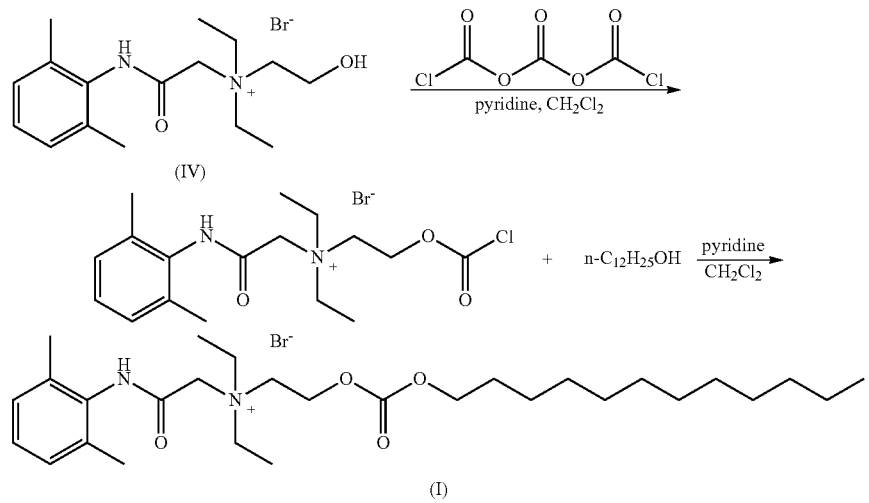

Referring to the method of Example 18, white powder solid was obtained, with a yield of 46%.

$^1$H NMR (400 MHz, CDCl$_3$) δ: 10.52 (br, 1H), 7.03~7.11 (m, 3H), 5.08 (s, 2H), 4.67 (t, J=4.6 Hz, 2H), 4.14 (t, J=6.8 Hz, 2H), 4.04~4.06 (m, 4H), 2.28 (s, 6H), 2.03 (br, 2H), 1.67 (t, J=6.8 Hz, 2H), 1.53 (t, J=7.2 Hz, 6H), 1.26~1.30 (m, 18H), 0.88 (t, J=6.8 Hz, 3H).

$^{13}$C NMR (100 MHz, CDCl$_3$) δ: 8.49, 14.14, 18.92, 22.70, 28.50, 29.19, 29.35, 29.49, 29.58, 29.64, 31.92, 56.57, 57.82, 57.87, 60.54, 69.32, 127.60, 128.18, 132.83, 135.11, 154.30, 161.76.

HRMS: [C$_{29}$H$_{51}$N$_2$O$_4$]$^+$, 491.3642.

Example 27

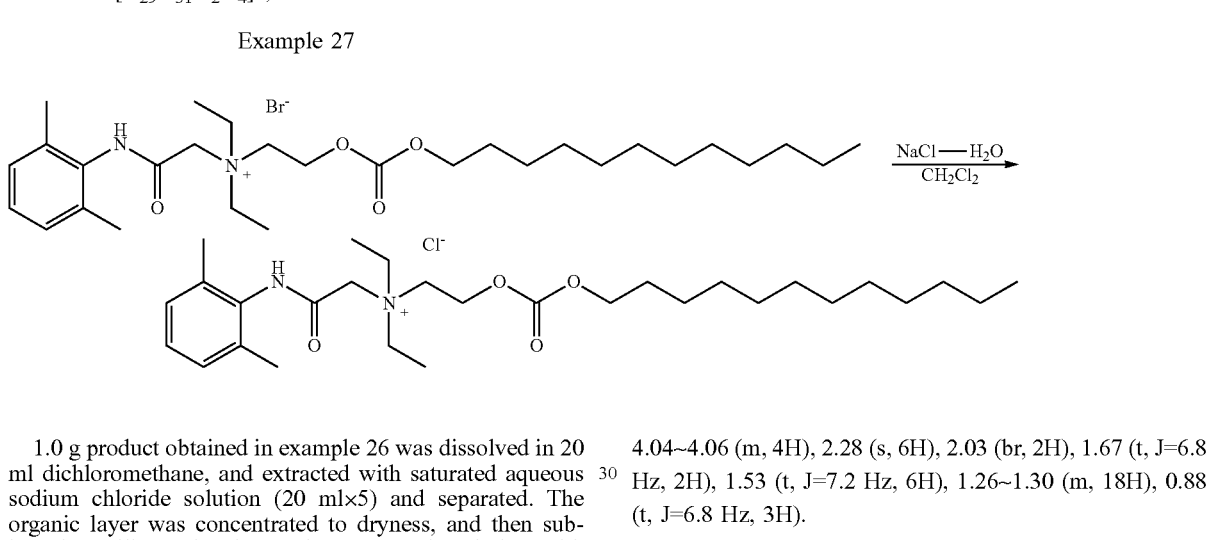

1.0 g product obtained in example 26 was dissolved in 20 ml dichloromethane, and extracted with saturated aqueous sodium chloride solution (20 ml×5) and separated. The organic layer was concentrated to dryness, and then subjected to silica gel column chromatography eluting with dichloromethane:methanol (20:1~5:1), to obtain white powder solid (1.0 g, yield 92%).

$^1$H NMR (400 MHz, CDCl$_3$) δ: 10.52 (br, 1H), 7.03~7.11 (m, 3H), 5.08 (s, 2H), J=4.6 Hz, 2H), 4.14 (t, J=6.8 Hz, 2H), 4.04~4.06 (m, 4H), 2.28 (s, 6H), 2.03 (br, 2H), 1.67 (t, J=6.8 Hz, 2H), 1.53 (t, J=7.2 Hz, 6H), 1.26~1.30 (m, 18H), 0.88 (t, J=6.8 Hz, 3H).

By detection with chromatography of ions, the content of chloridions was more than 99.9%.

Example 28

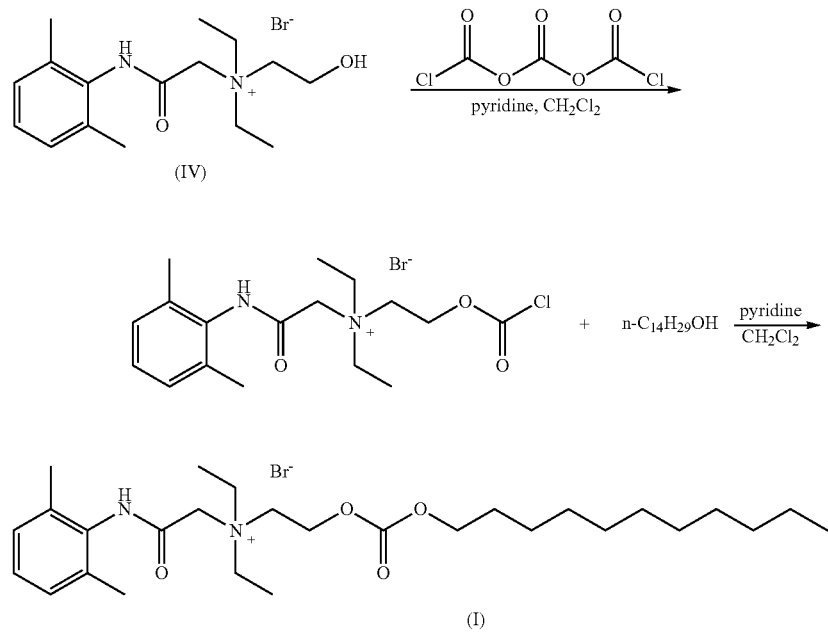

Referring to the method of Example 18, white powder solid was obtained, with a yield of 51%.

$^1$H NMR (400 MHz, CDCl$_3$) δ: 10.52 (br, 1H), 7.02~7.10 (m, 3H), 5.05 (s, 2H), 4.67 (t, J=4.4 Hz, 2H), 4.13 (t, J=6.8 Hz, 2H), 4.05~4.07 (m, 2H), 3.68~3.78 (m, 4H), 2.27 (s, 6H), 1.64 (t, J=6.9 Hz, 2H), 1.51 (t, J=7.2 Hz, 6H), 1.26~1.30 (m, 22H), 0.88 (t, J=6.8 Hz, 3H).

$^{13}$C NMR (100 MHz, CDCl$_3$) δ: 8.49, 14.13, 18.91, 22.69, 25.60, 28.50, 29.20, 29.36, 29.50, 29.57, 29.65, 29.67, 29.69, 31.92, 56.53, 57.80, 57.87, 60.59, 69.25, 76.76, 127.56, 128.16, 132.88, 135.12, 154.30, 161.79.

HRMS: [C$_{31}$H$_{55}$N$_2$O$_4$]$^+$, 519.4166.

Example 29

1.0 g product obtained in example 29 was dissolved in 20 ml dichloromethane, and extracted with saturated aqueous sodium chloride solution (20 ml×5) and separated. The organic layer was concentrated to dryness, and then subjected to silica gel column chromatography eluting with dichloromethane:methanol (20:1~5:1), to obtain white powder solid (1.0 g, yield 92%).

$^1$H NMR (400 MHz, CDCl$_3$) δ: 10.60 (br, 1H), 7.04~7.09 (m, 3H), 5.12 (s, 2H), 4.68 (t, J=4.5 Hz, 2H), 4.16 (t, J=6.8 Hz, 2H), 4.02~4.05 (m, 2H), 3.64~3.82 (m, 4H), 2.28 (s, 6H), 1.64~1.68 (m, 2H), 1.56 (t, J=7.2 Hz, 6H), 1.26~1.31 (m, 26H), 0.88 (t, J=6.4 Hz, 3H).

By detection with chromatography of ions, the content of chloridions was more than 99.9%.

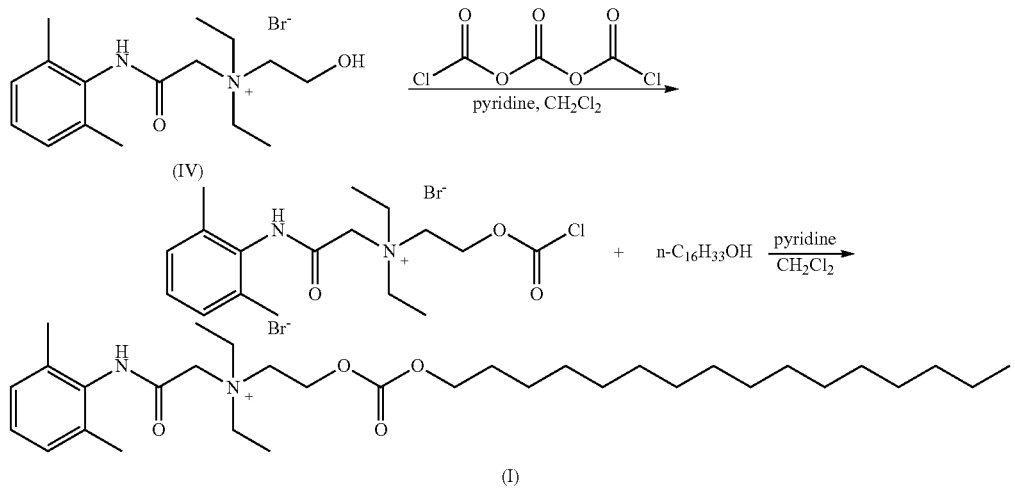

Referring to the method of Example 18, white powder solid was obtained, with a yield of 59%.

$^1$H NMR (400 MHz, CDCl$_3$) δ: 10.60 (br, 1H), 7.04~7.09 (m, 3H), 5.12 (s, 2H), 4.68 (t, J=4.5 Hz, 2H), 4.16 (t, J=6.8 Hz, 2H), 4.02~4.05 (m, 2H), 3.64~3.82 (m, 4H), 2.28 (s, 6H), 1.64~1.68 (m, 2H), 1.56 (t, J=7.2 Hz, 6H), 1.26~1.31 (m, 26H), 0.88 (t, J=6.4 Hz, 3H).

$^{13}$C NMR (100 MHz, CDCl$_3$) δ: 8.48, 14.13, 18.96, 22.70, 25.60, 28.51, 29.37, 29.49, 29.59, 29.70, 31.93, 56.63, 57.95, 60.48, 69.42, 127.63, 128.20, 132.78, 135.03, 154.27, 161.62.

HRMS: [C$_{33}$H$_{59}$N$_2$O$_4$]$^+$, 547.4478.

Example 30

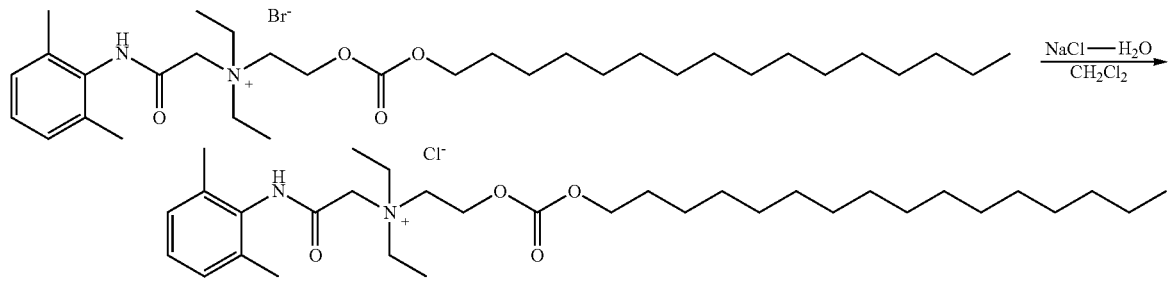

Example 31

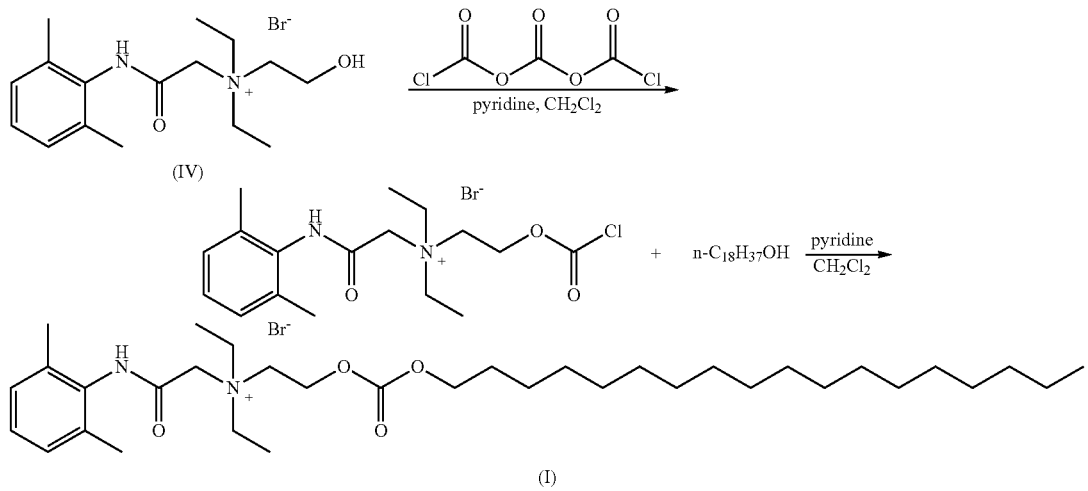

Referring to the method of Example 18, white powder solid was obtained, with a yield of 49%.

$^1$H NMR (400 MHz, CDCl$_3$) δ: 10.52 (br, 1H), 7.03~7.11 (m, 3H), 5.12 (s, 2H), 4.68 (t, J=4.6 Hz, 2H), 4.15 (t, J=6.8 Hz, 2H), 4.04~4.06 (m, 2H), 3.68~3.80 (m, 4H), 2.28 (s, 6H), 1.63~1.67 (m, 2H), 1.54 (t, J=7.2 Hz, 6H), 1.26~1.30 (m, 30H), 0.88 (t, J=6.6 Hz, 3H).

$^{13}$C NMR (100 MHz, CDCl$_3$) δ: 8.50, 14.14, 18.94, 22.70, 25.60, 28.50, 29.21, 29.37, 29.51, 29.60, 29.67, 29.71, 31.93, 56.58, 57.84, 57.80, 60.54, 69.33, 127.60, 128.19, 132.83, 135.10, 154.30, 161.74.

HRMS: [C$_{35}$H$_{63}$N$_2$O$_4$]$^+$, 575.4791.

Example 32

Referring to the method of Example 18, white powder solid was obtained, with a yield of 48%.

$^1$H NMR (400 MHz, CDCl$_3$) δ: 10.53 (br, 1H), 7.02~7.10 (m, 3H), 5.08 (s, 2H), 4.68 (t, J=4.5 Hz, 2H), 4.14 (t, J=6.8 Hz, 2H), 4.04~4.06 (m, 2H), 3.66~3.81 (m, 4H), 2.27 (s, 6H), 1.63~1.67 (m, 2H), 1.53 (t, J=7.2 Hz, 6H), 1.26~1.30 (m, 34H), 0.88 (t, J=6.6 Hz, 3H).

$^{13}$C NMR (100 MHz, CDCl$_3$) δ: 8.50, 14.14, 18.92, 22.70, 25.60, 28.51, 29.20, 29.37, 29.51, 29.61, 29.67, 29.72, 31.93, 56.57, 57.83, 60.56, 69.30, 127.58, 128.18, 132.85, 135.10, 154.30, 161.76.

HRMS: [C$_{37}$H$_{67}$N$_2$O$_4$]$^+$, 603.5096.

Example 33

To penicillin bottle containing 5 mmol product obtained in Example 14, was added 1 ml distilled water, and shaken at 40° C., to obtain an uniform transparent solution.

By TEM detection, the particle diameter of micelle was 40-70 nm, as shown in FIG. 1.

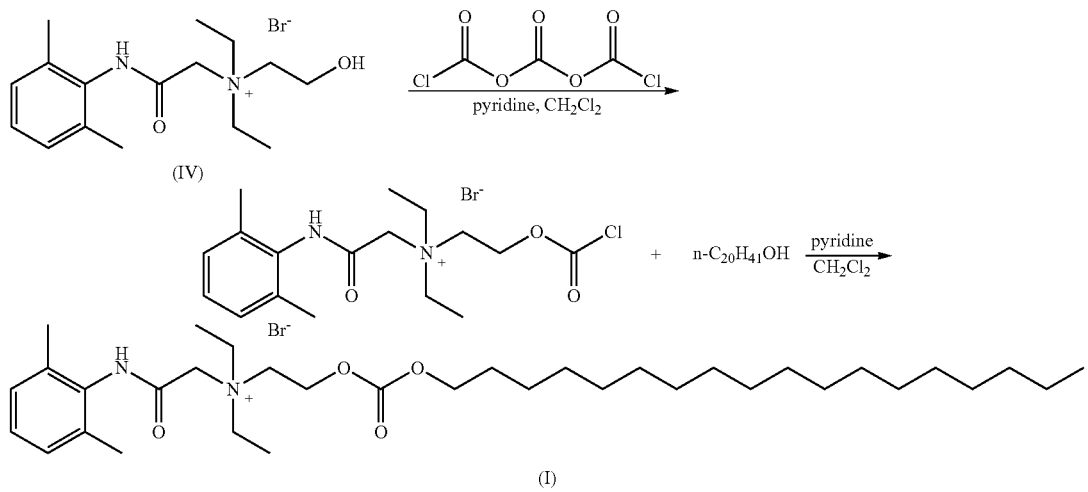

Example 34

To penicillin bottle containing 5 mmol product obtained in Example 19, was added 1 ml physiological saline, and shaken at 40° C., to obtain an uniform transparent solution.

Figure 2:
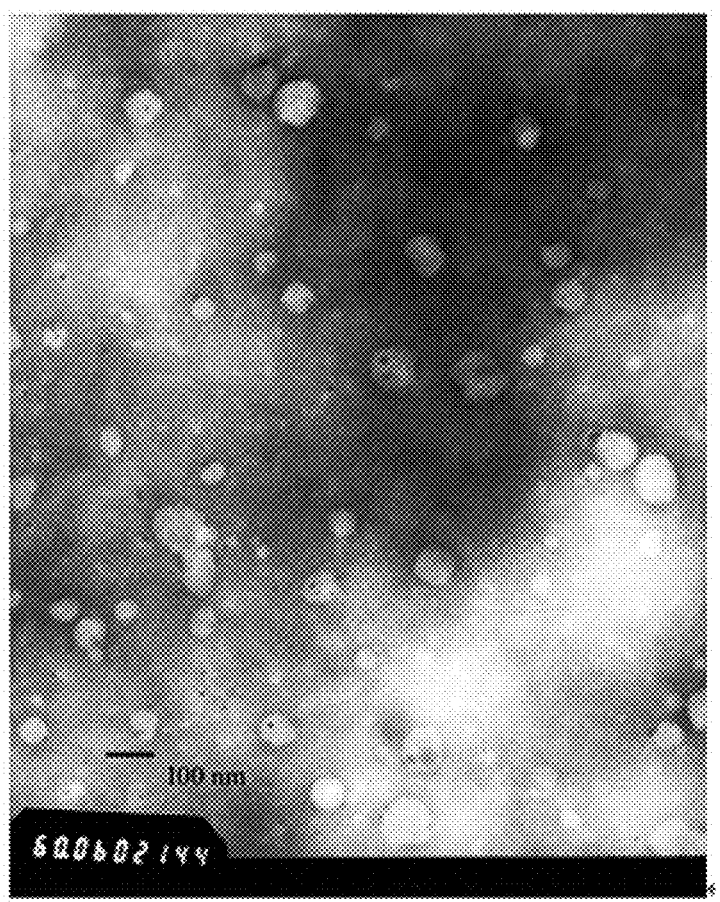
FIG. 2 Transmission electron microscopy image of formed micelle.

By TEM detection, the particle diameter of micelle was 40-70 nm, as shown in FIG. 2.

Example 35

To penicillin bottle containing 5 mmol product obtained in Example 22, was added 1 ml 5% ethanol solution, and shaken at 40° C., to obtain an uniform transparent solution.

Figure 3:
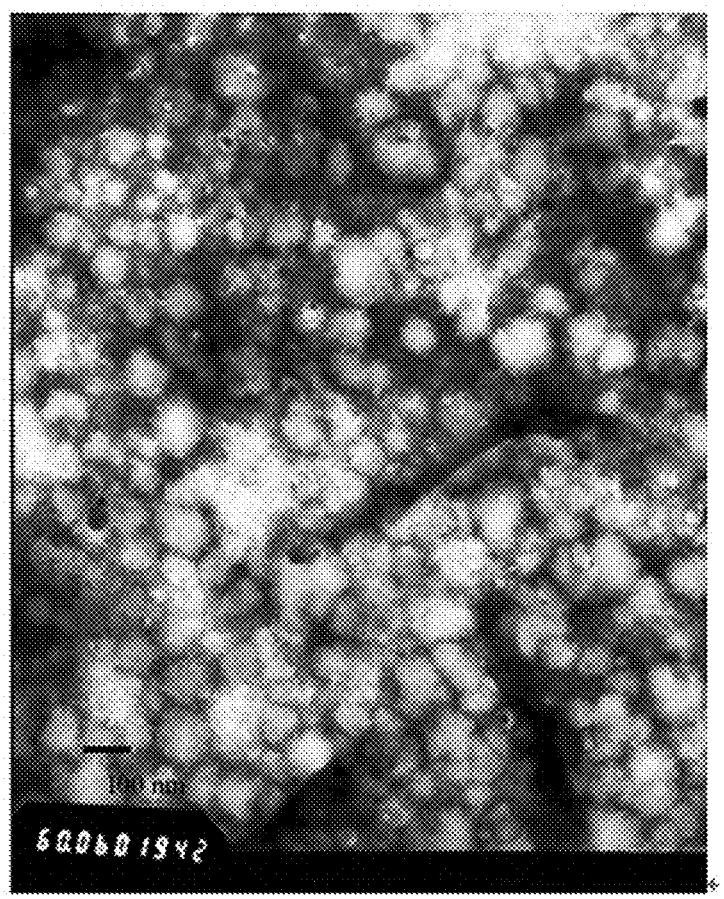
FIG. 3 Transmission electron microscopy image of formed micelle.

By TEM detection, the particle diameter of micelle was 40-80 nm, as shown in FIG. 3.

Example 36

To penicillin bottle containing 5 mmol product obtained in Example 24, was added 1 ml 5% 1,2-propylene glycol solution, and shaken at 40° C., to obtain an uniform transparent solution.

Figure 4:
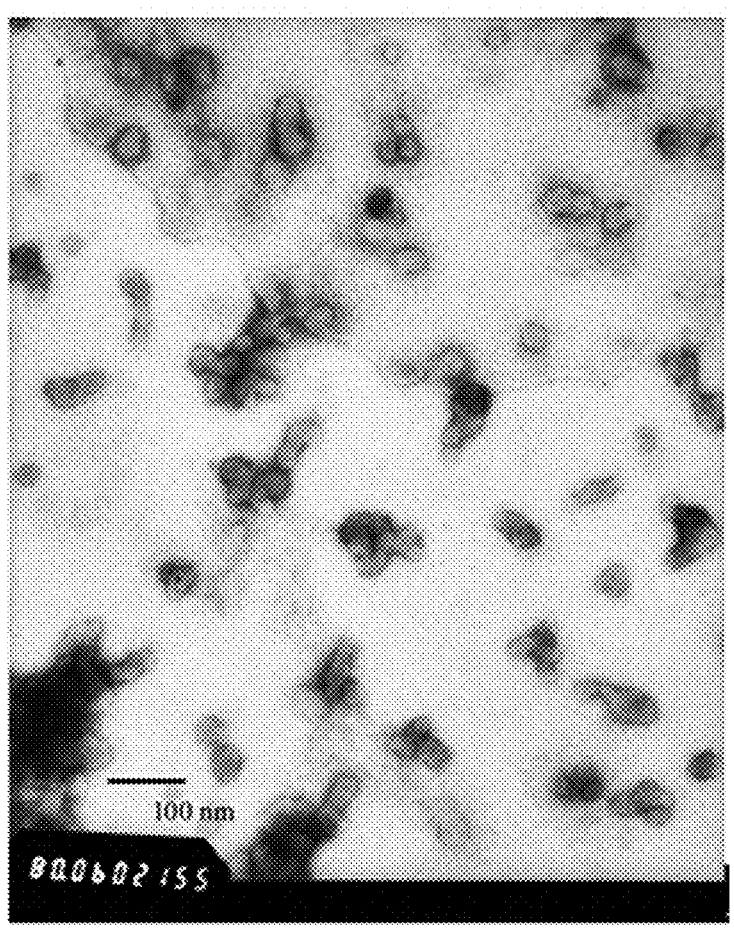
FIG. 4 Transmission electron microscopy image of formed micelle.

By TEM detection, the particle diameter of micelle, produced by self-assembly of products in solvent, was 20-30 nm, as shown in FIG. 4.

Example 37

To penicillin bottle containing 5 mmol product obtained in Example 15, was added 1 ml 5% 1,2-propylene glycol solution, and shaken at 40° C., to obtain an uniform transparent solution.

By TEM detection, micelle was produced by self-assembly of products in solvent.

Example 38

To penicillin bottle containing 5 mmol product obtained in Example 15, was added 1 ml 5% glycerol solution, and shaken at 40° C., to obtain an uniform transparent solution.

By TEM detection, products of example 15 self-assembled into micelle in solvent.

Example 39

To penicillin bottle containing 5 mmol product obtained in Example 15 and 3 mmol procaine, was added 1 ml 5% ethanol solution, and shaken at 40° C., to obtain an uniform transparent solution.

By TEM detection, products of example 15 self-assembled into micelle in solvent.

Example 40

To penicillin bottle containing 5 mmol product obtained in Example 15 and 3 mmol lidocaine, was added 1 ml 5% ethanol solution, and shaken at 40° C., to obtain an uniform transparent solution.

By TEM detection, products of example 15 self-assembled into micelle in solvent.

Example 41

To penicillin bottle containing 25 mmol product obtained in Example 17 and 3 mmol bupivacaine, was added 1 ml 5% ethanol solution, and shaken at 40° C., to obtain an uniform transparent solution.

Figure 5:
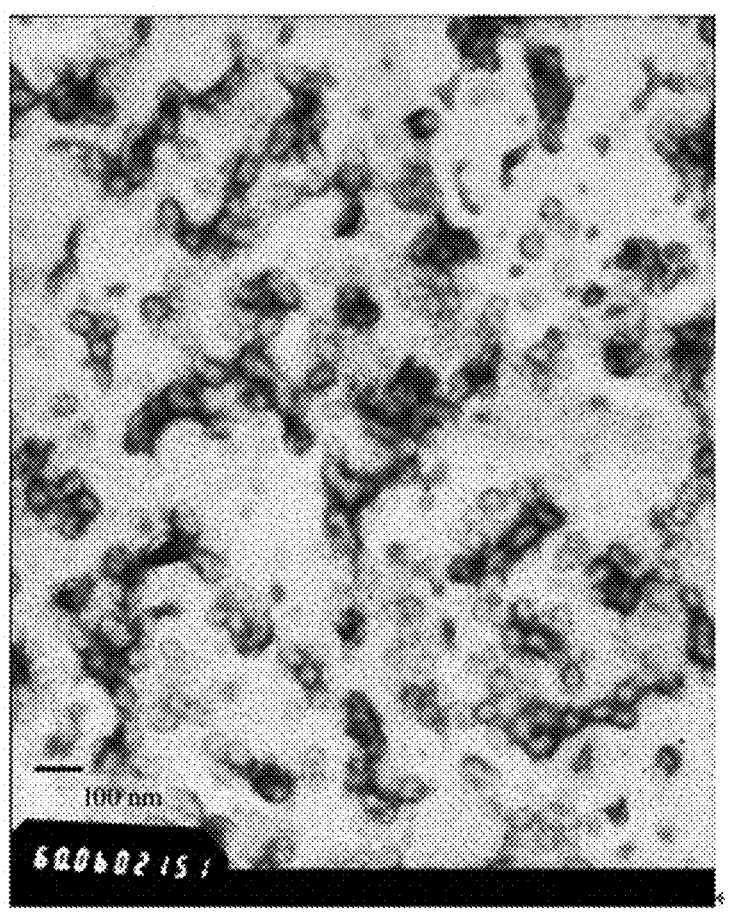
FIG. 5 Transmission electron microscopy image of formed micelle.

By TEM detection, products self-assembled into micelle in solvent, as shown in FIG. 5.

Example 42

To penicillin bottle containing 25 mmol product obtained in Example 18 and 3 mmol ropivacaine, was added 1 ml 5% ethanol solution, and shaken at 40° C., to obtain an uniform transparent solution.

Figure 6:
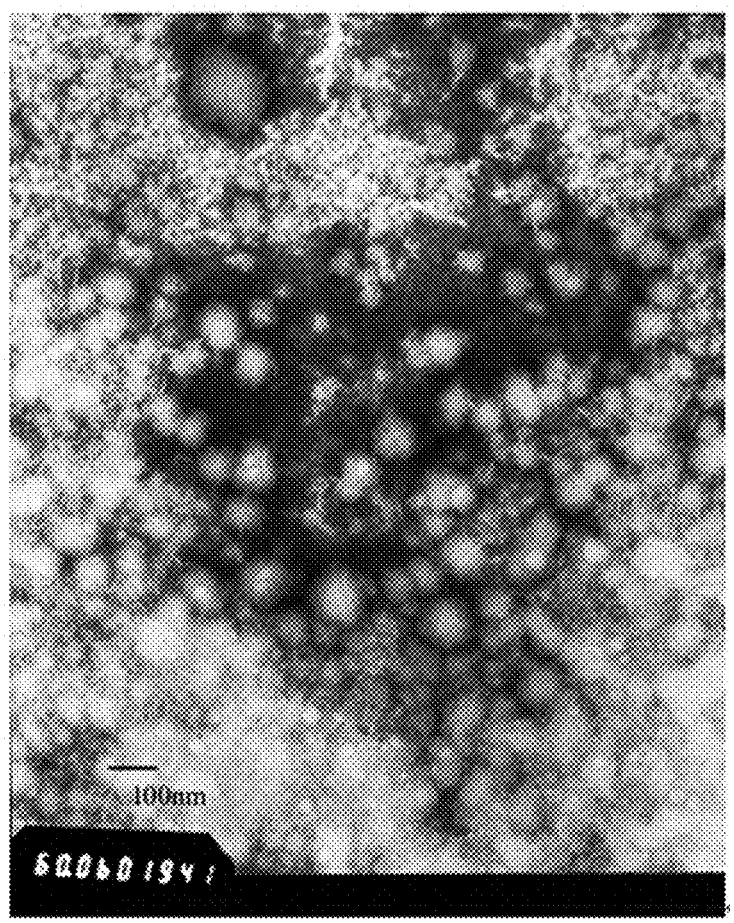
FIG. 6 Transmission electron microscopy image of formed micelle.

By TEM detection, products of Example 18 self-assembled into micelle in solvent, as shown in FIG. 6.

Example 43

To penicillin bottle containing 25 mmol product obtained in Example 15 and 3 mmol capsaicin, was added 2 ml 5% ethanol solution, and shaken at 40° C., to obtain an uniform transparent solution.

Figure 7:
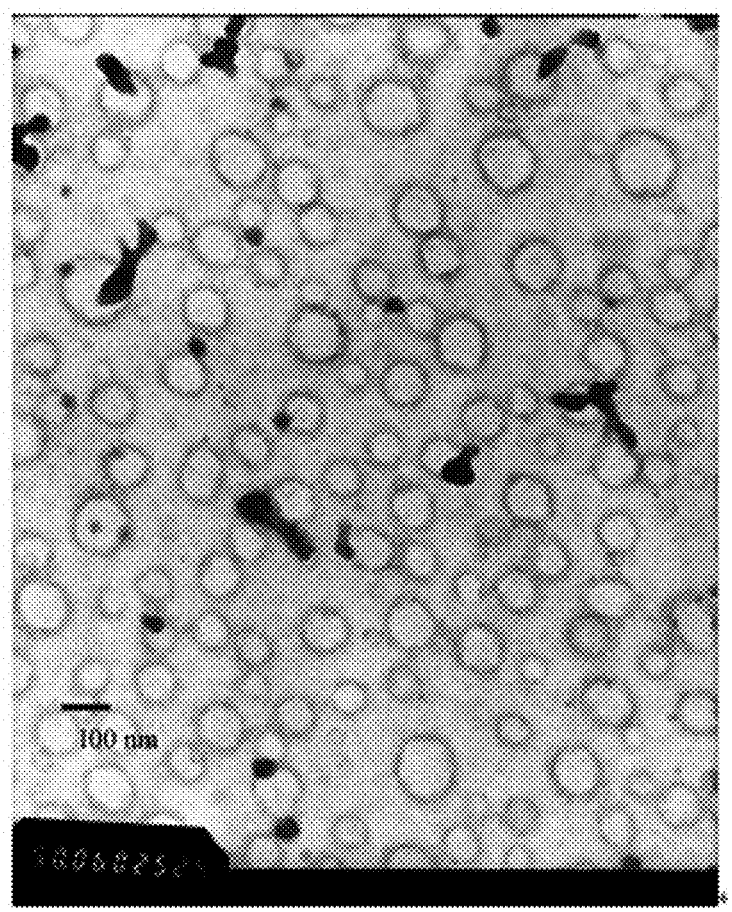
FIG. 7 Transmission electron microscopy image of formed micelle.

By TEM detection, products of Example 15 self-assembled into micelle in solvent, as shown in FIG. 7.

Example 44

To penicillin bottle containing 25 mmol product obtained in Example 15 and 3 mmol 4-hydroxy-3-methoxybenzyl nonanoate, was added 2 ml 5% ethanol solution, and shaken at 40° C., to obtain an uniform transparent solution.

Figure 8:
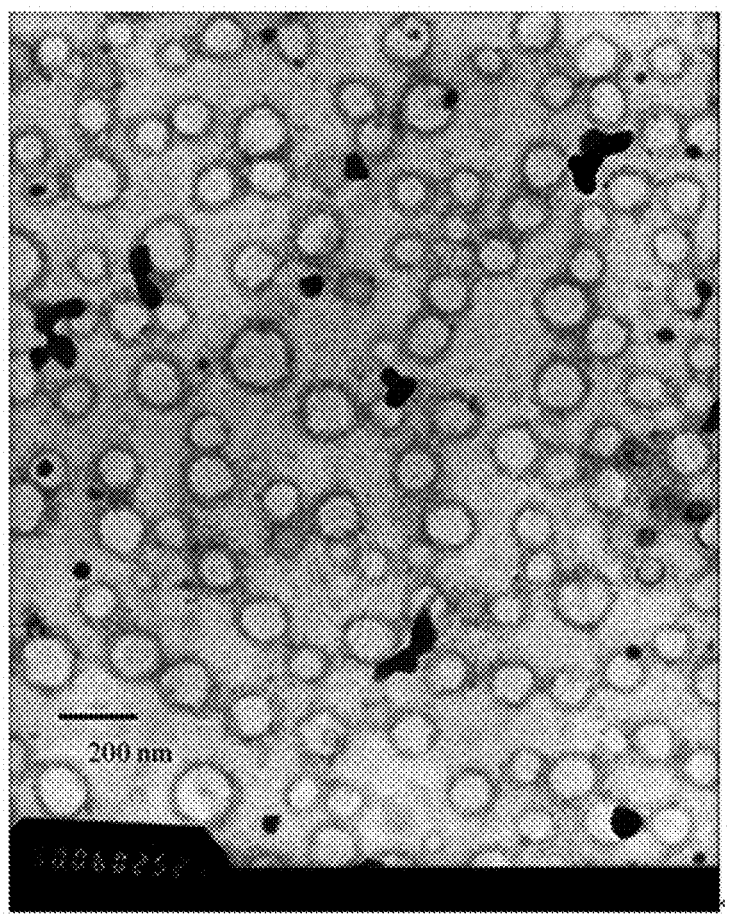
FIG. 8 Transmission electron microscopy image of formed micelle.

By TEM detection, products of Example 15 self-assembled into micelle in solvent, as shown in FIG. 8.

Example 45

To PV tube containing 25 mmol product obtained in Example 7, was added 1 ml water, and shaken at 40° C., to obtain an uniform transparent solution.

Figure 9:
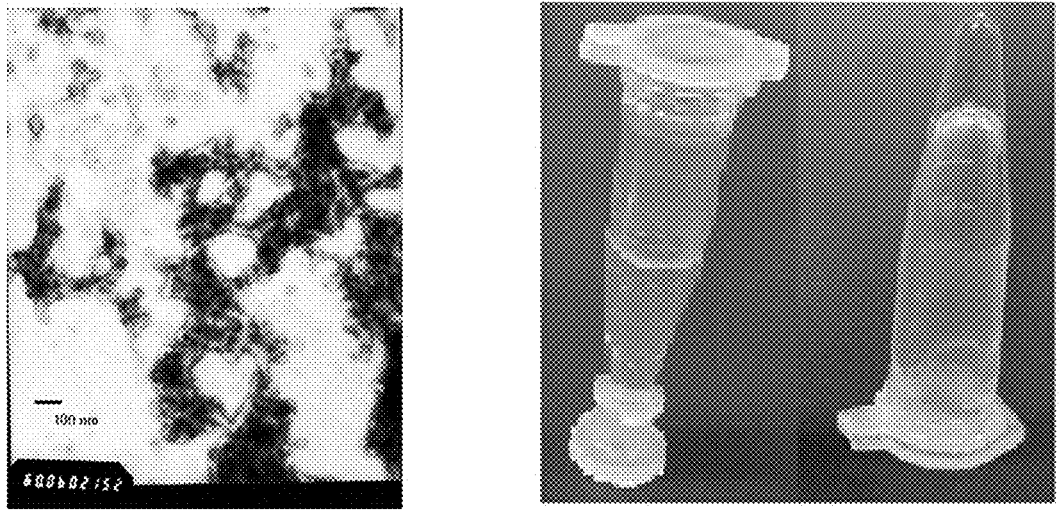
FIG. 9 Left picture: Transmission electron microscopy image of formed hydrogel; Right picture: formed hydrogel is subjected to 180° inversion, standing, and the flowability decreases.

By TEM detection, products self-assembled into accumulated lamellar micelle in water and thus formed gel, as shown in FIG. 9. Left picture in FIG. 9 showed products self-assembled into accumulated lamellar micelle in water; Right picture indicated that products formed hydrogel at room temperature, with flowability being obviously decreased, and by 180° inversion and standing, hydrogel could still partly keep old gel shape.

Example 46

To PV tube containing 25 mmol product obtained in Example 19, was added 1 ml water, and shaken at 40° C., to obtain an uniform transparent solution.

Figure 10:
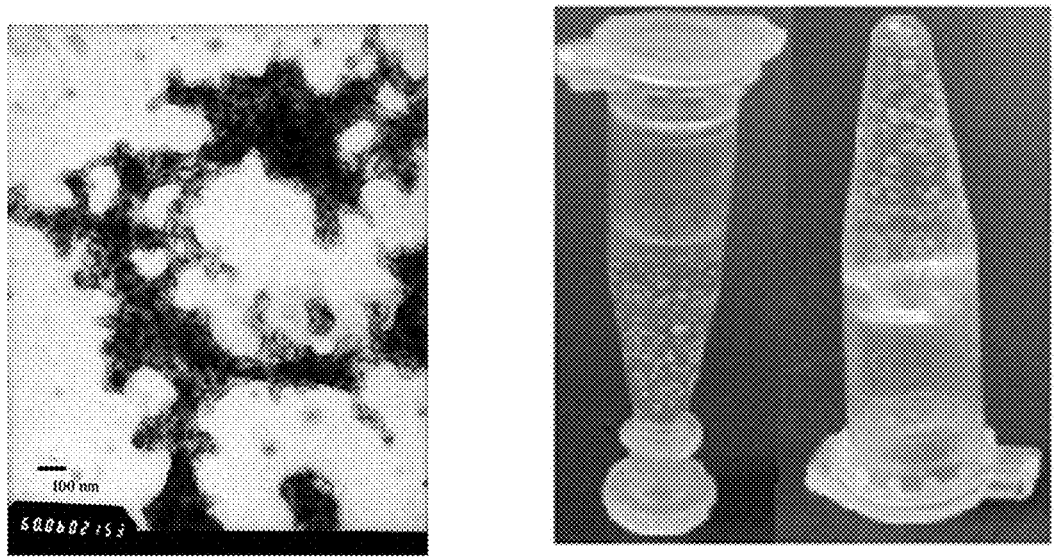
FIG. 10 Left picture: Transmission electron microscopy image of formed hydrogels; Right picture: formed hydrogel is subjected to 180° inversion, standing, and keeps old shape.

By TEM detection, products self-assembled into accumulated lamellar micelle in solvent and thus formed gel, as shown in FIG. 10. Left picture in FIG. 10 showed products self-assembled into accumulated lamellar micelle in water; right picture indicated that products formed hydrogel at room temperature, with flowability being obviously decreased, and by 180° inversion and standing, hydrogel could still partly keep old gel shape.

Example 47

To PV tube containing 25 mmol product obtained in Example 22, was added 1 ml water, and shaken at 40° C., to obtain an uniform transparent solution.

Figure 11:
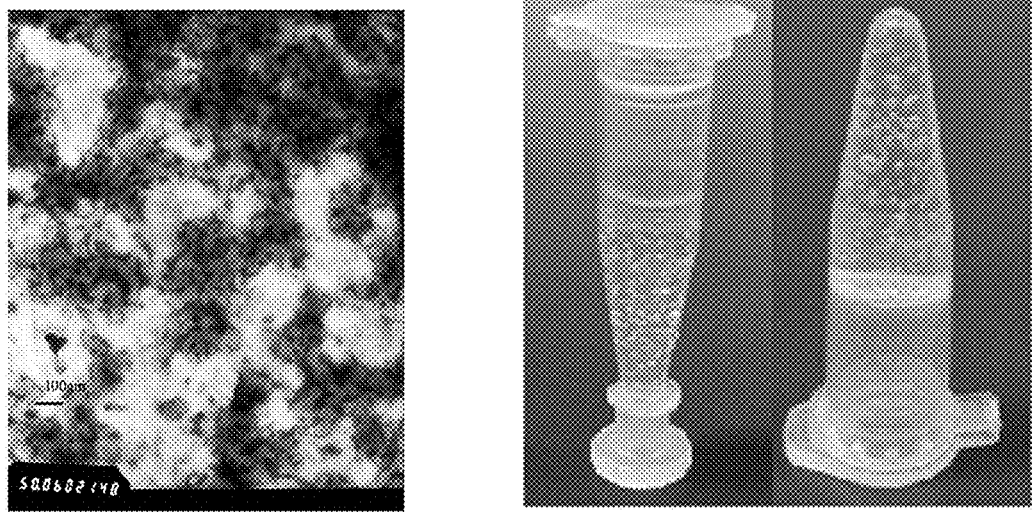
FIG. 11 Left picture: Transmission electron microscopy image of formed hydrogel; Right picture: formed hydrogel is subjected to 180° inversion, standing, and keeps old shape.

By TEM detection, products self-assembled into accumulated lamellar micelle in solvent and thus formed gel, as shown in FIG. 11. Left picture in FIG. 11 showed products self-assembled into accumulated lamellar micelle in water;

right picture indicated that products formed hydrogel at room temperature, with flowability being obviously decreased, and by 180° inversion and standing, hydrogel could still partly keep old gel shape.

Example 48

To PV tube containing 25 mmol product obtained in Example 26, was added 1 ml water, and shaken at 40° C., to obtain an uniform transparent solution.

Figure 12:
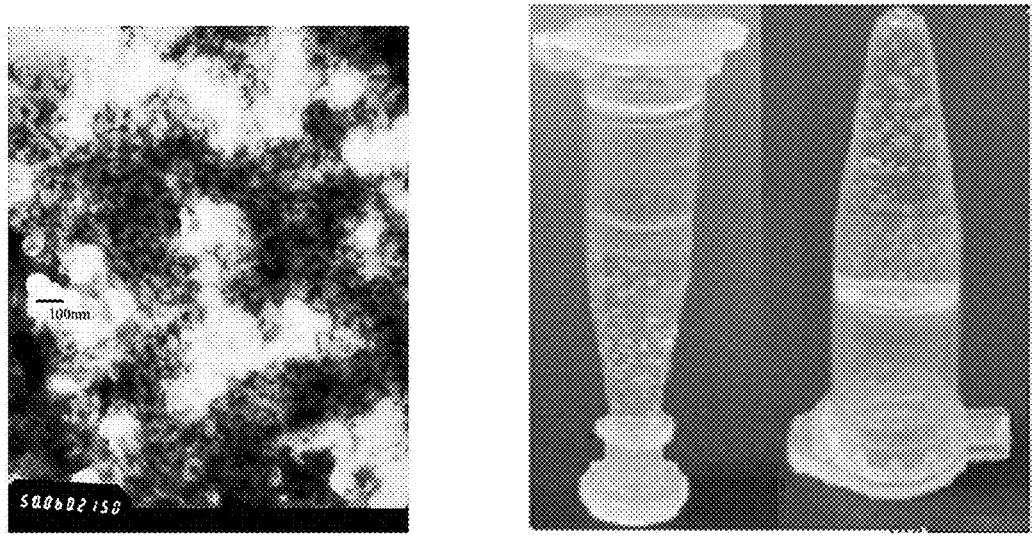
FIG. 12 Left picture: Transmission electron microscopy image of formed hydrogel; Right picture: formed hydrogel is subjected to 180° inversion, standing, and keeps old shape.

By TEM detection, products self-assembled into accumulated lamellar micelle in solvent and thus formed gel, as shown in FIG. 12. Left picture in FIG. 12 showed products self-assembled into accumulated lamellar micelle in water; right picture indicated that products formed hydrogel at room temperature, with flowability being obviously decreased, and by 180° inversion and standing, hydrogel could still partly keep old gel shape.

Example 49

To penicillin bottle containing 25 mmol product obtained in Example 26, was added 1 ml normal saline, and shaken at 40° C., to obtain an uniform transparent solution.

By TEM detection, products of Example 26 self-assembled into gel in solvent.

Example 50

To penicillin bottle containing 25 mmol product obtained in Example 26, was added 1 ml 5% ethanol solution, and shaken at 40° C., to obtain an uniform transparent gel.

By TEM detection, products of Example 26 self-assembled into gel in solvent.

Example 51

To penicillin bottle containing 25 mmol product obtained in Example 26, was added 1 ml 5% 1,2-propylene glycol solution, and shaken at 40° C., to obtain an uniform transparent gel.

By TEM detection, products of Example 26 self-assembled into gel in solvent.

Example 52

To penicillin bottle containing 25 mmol product obtained in Example 26, was added 1 ml 5% glycerol solution, and shaken at 40° C., to obtain an uniform transparent gel.

By TEM detection, products of Example 26 self-assembled into gel in solvent.

Example 53

To penicillin bottle containing 25 mmol product obtained in Example 26 and 3 mmol procaine, was added 1 ml 5% ethanol solution, and shaken at 40° C., to obtain an uniform transparent gel.

By TEM detection, products of Example 26 self-assembled into gel in solvent.

Example 54

To penicillin bottle containing 25 mmol product obtained in Example 26 and 3 mmol lidocaine, was added 1 ml 5% ethanol solution, and shaken at 40° C., to obtain an uniform transparent gel.

By TEM detection, products of Example 26 self-assembled into gel in solvent.

Example 55

To penicillin bottle containing 25 mmol product obtained in Example 26 and 3 mmol bupivacaine, was added 1 ml 5% ethanol solution, and shaken at 40° C., to obtain an uniform transparent gel.

By TEM detection, products of Example 26 self-assembled into gel in solvent.

Example 56

To penicillin bottle containing 25 mmol product obtained in Example 26 and 3 mmol ropivacaine, was added 1 ml 5% ethanol solution, and shaken at 40° C., to obtain an uniform transparent gel.

By TEM detection, products of Example 26 self-assembled into gel in solvent.

Example 57

To penicillin bottle containing 25 mmol product obtained in Example 26 and 10 mg capsaicin, was added 1 ml 5% ethanol solution, and shaken at 40° C., to obtain an uniform transparent gel.

By TEM detection, products of Example 26 self-assembled into gel in solvent.

Example 58

To penicillin bottle containing 25 mmol product obtained in Example 26 and 10 mg 4-hydroxy-3-methoxybenzyl nonanoate, was added 1 ml 5% ethanol solution, and shaken at 40° C., to obtain an uniform transparent gel.

By TEM detection, products of Example 26 self-assembled into gel in solvent.

Example 59

To penicillin bottle containing products obtained in Example 26 and 10 mg 4-hydroxy-3-methoxybenzyl nonanoate, was added 2 ml 5% ethanol solution, and shaken at 40° C., to obtain an uniform transparent gel.

By TEM detection, products of Example 26 self-assembled into gel in solvent.

Example 60

The solutions of products obtained in Examples 3-32 were prepared, as the method of Example 33, and kept for use.

Selected above micelle, positive control lidocaine, and negative control normal saline were respectively administrated to 28 groups of test rats fully adapted to experiment environment, with five rats for each group. The administration dosage is: the concentration of lidocaine group being 2% aqueous solution (84 mmol/L), and the concentration of tested drug being 5 mmol/L. The injection volume of each rat receiving drugs or the control was 0.2 ml, and the drug or the control was injected to close to sciatic nerve of rats by guidance of nerve locator.

Specific procedures and the evaluation criterion for local anesthetic effect were as follows:
Blocking of Sciatic Nerve The tested rats were placed on bench board and allowed to inhale 5% isoflurane. After body-righting reflex abolition, rats are allowed to continue inhaling 1.5% isoflurane, to keep anesthesia. Keeping left-lateral position, their corresponding injection area sacrococygeal region was shaved, then routine sterilization and draping were performed. Two osseous anatomic landmarks greater trochanter of femur and tuber is chiadicum were laid hands, and the middle point of this line was the needle insertion position. If skin was taut, 1 ml injector was inserted along perpendicular of skin. When needlepoint reached hucklebone, the insertion was finished. Once no blood return was found as suction, 0.2 ml drug solution was slowly injected. Needle was lifted, and isoflurane was shut off. Animals were placed in observation cage until they naturally awakened.

Observation of Effect on Serve Blocking:

10 min, 30 min, 60 min after injection, and afterward one hour per 4 hours, then two hour per 12 h, 18 h, 24 h, till five days, two persons investigated the following ethology of rats, who did not know about the treatment of rats.

Mechanical Withdrawal Threshold (VFH):

Rats were placed in transparent observation cages with a bottom of smooth metal sieve plate, and the corrected von frey filament was used to stimulate the foot lateral skin of rats (innervated region of sciatic nerve) from down to up. Von frey filaments were used from 0.4 g, and gradually increased to 60 g. For each stimulation, slightly bent of filament was used as a standard, or rats moved aside this side of limbs. Otherwise, once the stimulation time reached 3 s, operator stopped stimulating. Three tests were carried out for each time point, and the interval between two tests was 5 min, to avoid sensibilization.

If the mechanical withdrawal threshold value was more than 60 g, the nerve blocking was considered as effective. The interval from completion of injection to the time point obtaining the first mechanical withdrawal threshold value of above 60 g was the effective time of the mechanical pain sensation blocking; the interval from completion of injection to the time that the mechanical withdrawal threshold value firstly decreased to less than 60 g was the ineffective time of the mechanical pain sensation blocking; their difference was the hold time of the mechanical pain sensation blocking.

Motor Function:

The hindlimb postural extensor thrust (PET) was used for evaluation. Rats were lifted vertically and their hindlimbs of injection side stepped on the top of electronic balance. At this time, the postural extensor thrust was shown as the value of balance. When limbs were completely paralytic, the digital reading was the weight of limbs, about 20 g. If the test value was more than half of the difference between the baseline and the limbs weight, the motor function was taken as recovery; If less than or equal to half of the difference, the motor function was taken as deprivation.

The interval between completion of injection and the time point that the motor function was firstly deprivated was the time of effective motor blocking; the interval between completion of injection and the time point that the motor function was firstly recovered was the time of ineffective motor blocking; their difference was the hold time of motor blocking.

TABLE 1

First local anesthetic experiment of rats.

| Test drugs | Effective local anesthetic time | The hold time of sensation blocking | The hold time of motor blocking |
| --- | --- | --- | --- |
| Example3product | 20 min | 7 h | 7 h |
| Example4product | 20 min | 8 h | 8 h |
| Example5product | 18 min | 8 h | 8 h |
| Example6product | 20 min | 72 h | 72 h |
| Example7product | 20 min | 75 h | 70 h |
| Example8product | 18 min | 73 h | 70 h |
| Example9product | 20 min | 80 h | 80 h |
| Example10product | 20 min | 81 h | 81 h |
| Example11product | 20 min | 82 h | 82 h |
| Example12product | 20 min | 80 h | 80 h |
| Example13product | 19 min | 79 h | 79 h |
| Example14product | 15 min | 82 h | 70 h |
| Example15product | 17 min | 81 h | 66 h |
| Example16product | 18 min | 85 h | 62 h |
| Example17product | 16 min | 82 h | 62 h |
| Example18product | 16 min | 88 h | 60 h |
| Example19product | 16 min | 82 h | 56 h |
| Example20product | 18 min | 83 h | 55 h |
| Example21product | 18 min | 82 h | 60 h |
| Example22product | 18 min | 81 h | 61 h |
| Example23product | 20 min | 82 h | 62 h |
| Example24product | 20 min | 82 h | 75 h |
| Example25product | 20 min | 81 h | 80 h |
| Example26product | 20 min | 80 h | 80 h |
| Example27product | 20 min | 78 h | 80 h |
| Example28product | 20 min | 76 h | 79 h |
| Example29product | 20 min | 78 h | 80 h |
| Example30product | 19 min | 74 h | 78 h |
| Example31product | 20 min | 78 h | 80 h |
| Example32product | 20 min | 78 h | 80 h |
| 2% lidocaine hydrochloride | 1 min | 2 h | 2 h |

The above experimental results indicated that products of Examples 3-5 can produce the local anesthesia effect lasting more than 7 hours; products of Examples 6-32 can produce the local anesthesia effect lasting more than 72 hours.

Example 61

The solution of products obtained in Example 18 was prepared, as the method of Examples 33-35 and 41-48, and kept for use.

Selected above solution, positive control lidocaine, and negative control normal saline were respectively administrated to 12 groups of test rats fully adapted to experiment environment, with five rats for each group. The administration dosage is: the concentration of lidocaine group being 2% aqueous solution (84 mmol/L). The injection volume of each rat receiving drugs or the control was 0.2 ml, and the drug or the control was injected to close to sciatic nerve of rats by guidance of nerve locator.

Specific procedures and the evaluation criterion for local anesthetic effect were same as mentioned in Example 60.

The local anesthetic effect was shown in Table 2.

TABLE 2

Second local anesthetic experiment of rats

| Test drugs | Effective local anesthetic time | The hold time of sensation blocking | The hold time of motor blocking |
| --- | --- | --- | --- |
| Example33product | 20 min | 75 h | 72 h |
| Example34product | 20 min | 75 h | 70 h |

TABLE 2-continued

Second local anesthetic experiment of rats

| Test drugs | Effective local anesthetic time | The hold time of sensation blocking | The hold time of motor blocking |
| --- | --- | --- | --- |
| Example35product | 18 min | 74 h | 72 h |
| Example36product | 20 min | 82 h | 82 h |
| Example37product | 20 min | 85 h | 82 h |
| Example38product | 19 min | 83 h | 79 h |
| Example39product | 20 min | 82 h | 82 h |
| Example40product | 20 min | 85 h | 82 h |
| Example41product | 5 min | 80 h | 40 h |
| Example42product | 5 min | 81 h | 31 h |
| Example43product | 5 min | 81 h | 11 h |
| Example44product | 5 min | 81 h | 20 h |
| 2% lidocaine hydrochloride | 1 min | 2 h | 2 h |

The above experimental results indicated this type of drugs can produce the local anesthetic effect lasting more than 72 hours.

Example 62

25 mmol/L transparent uniform hydrogels of products obtained in Examples 7-10 and 13-32 were prepared under sterile conditions, as the method of Example 45, and kept for use.

Above hydrogels, positive control lidocaine, and negative control normal saline were respectively administrated to 35 groups of test rats fully adapted to experiment environment, with five rats for each group. The administration dosage is: the concentration of lidocaine group being 2% aqueous solution (84 mmol/L). The injection volume of each rat receiving drugs or the control was 0.2 g, and the control was injected to near the sciatic nerve of rats by guidance of nerve locator; by surgery, the gels were embedded near the sciatic nerve of experimental rats after general anesthesia using sevoflurane. Specific procedures and the evaluation criterion for local anesthetic effect were same as mentioned in Example 60.

After awake, the local anesthetic effect was shown in Table 3.

TABLE 3

The third local anesthetic experiment of rats

| Test drugs | Effective local anesthetic time | The hold time of sensation blocking | The hold time of motor blocking |
| --- | --- | --- | --- |
| Example7product | 60 min | 90 h | 80 h |
| Example8product | 70 min | 92 h | 82 h |
| Example9product | 75 min | 98 h | 80 h |
| Example10product | 85 min | 80 h | 72 h |
| Example13product | 45 min | 80 h | 76 h |
| Example14product | 45 min | 81 h | 76 h |
| Example15product | 53 min | 81 h | 79 h |
| Example16product | 56 min | 82 h | 82 h |
| Example17product | 63 min | 85 h | 82 h |
| Example18product | 60 min | 83 h | 79 h |
| Example19product | 65 min | 90 h | 88 h |
| Example20product | 68 min | 92 h | 80 h |
| Example21product | 75 min | 88 h | 79 h |
| Example22product | 78 min | 95 h | 87 h |
| Example23product | 80 min | 92 h | 76 h |
| Example24product | 78 min | 87 h | 79 h |
| Example25product | 82 min | 83 h | 79 h |

TABLE 3-continued

The third local anesthetic experiment of rats

| Test drugs | Effective local anesthetic time | The hold time of sensation blocking | The hold time of motor blocking |
| --- | --- | --- | --- |
| Example26product | 88 min | 81 h | 77 h |
| Example27product | 90 min | 83 h | 76 h |
| Example28product | 88 min | 83 h | 79 h |
| Example29product | 92 min | 86 h | 84 h |
| Example30product | 95 min | 87 h | 86 h |
| Example31product | 92 min | 83 h | 78 h |
| Example32product | 98 min | 72 h | 70 h |
| 2% lidocaine hydrochloride | 1 min | 2 h | 2 h |

The above experimental results indicated this type of drugs can produce the local anesthetic effect lasting more than 72 hours.

The invention claimed is:

1. A long-chain dimethylaniline derivative compound having a structure represented by formula (I):

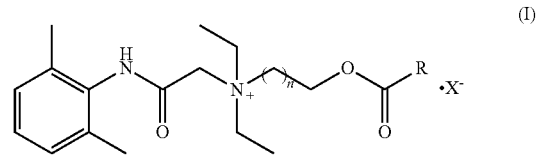

wherein X is selected from the group consisting of halogens and pharmaceutically acceptable anions; R is selected from the group consisting of straight chain or branch chain, substituted or unsubstituted, saturated or unsaturated $C_{2-30}$ alkyls and alkoxys; n represents an integer selected from the group consisting of 1, 2, 3, and 4.

2. The long-chain dimethylaniline derivative compound according to claim 1, wherein R in the structure of formula (I) is $C_{12-30}$ alkyls or alkoxys; n=1.

3. The long-chain dimethylaniline derivative compound according to claim 1, wherein R in the structure of formula (I) is $C_{2-11}$ alkoxys or alkyls; n=1.

4. A method for preparing a long-chain dimethylaniline derivative compound according to claim 1, represented by formula (I), comprising:

reacting compound (IV) with corresponding raw material straight chain or branch chain $C_{2-30}$ alkanols or carboxylic acids (V) to obtain the target compound (I) according to the following reaction

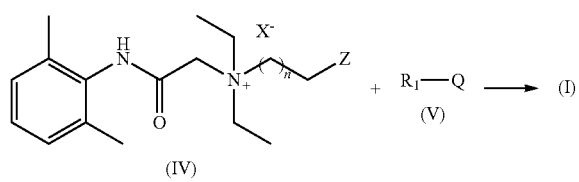

wherein X is selected from the group consisting of halogens and pharmaceutically acceptable anions; $R_1$ is selected from the group consisting of straight chain or branch chain, substituted or unsubstituted, saturated or unsaturated $C_{2-30}$ alkyls and alkoxys; Q represents OH, COOH, or COCl; Z represents OH or OCOCl; and n represents an integer selected from the group consisting of 1, 2, 3, and 4.

5. The long-chain dimethylaniline derivative compound according to claim 1, wherein said compound forms a micelle texture by self-assembly in the presence of water or an aqueous solvent.

6. The long-chain dimethylaniline derivative compound according to claim 5, wherein said aqueous solvent is a physiological saline or an organic solvent comprising ethanol, 1,2-propylene glycol, or glycerol.

7. The long-chain dimethylaniline derivative compound according to claim 5, wherein said micelle texture formed by self-assembly is a uniform stable hydrogel.

8. The long-chain dimethylaniline derivative compound according to claim 1, wherein said compound is an ingredient in a local anesthetic, an analgesic, and an antipruritic agent.

9. The long-chain dimethylaniline derivatives compound according to claim 5, wherein the micelle texture formed by self-assembly is an ingredient in biomaterials and/or carriers of medicinal package adjuvants or in a delivery system.

10. A method of preparing a medicament with long-acting local anesthetic effects, comprising:
    combining the long-chain dimethylaniline derivative compound according to claim 1 with one or more compound selected from the group consisting of procaine, lidocaine, bupivacaine, and ropivacaine, thereby forming a micelle texture; and
    combining the formed micelle texture with one or more active compound of transient acceptor cation channel agonist to form the medicament with long-acting local anesthetic effects.

11. The method of claim 10, wherein the active compound of transient acceptor cation channel agonist is selected from the group consisting of TRPV1 and/or TRPS, capsaicin, 4-hydroxy-3-methoxybenzyl nonanoate, 4-hydroxy-3-methoxybenzyl nonanoate, and eugenol.

* * * * *